US010342724B2

(12) United States Patent
Choi et al.

(10) Patent No.: US 10,342,724 B2
(45) Date of Patent: Jul. 9, 2019

(54) JOINT ASSEMBLY AND WALKING ASSISTANCE ROBOT

(71) Applicant: Samsung Electronics Co., Ltd., Suwon-si, Gyeonggi-do (KR)

(72) Inventors: Byungjune Choi, Gunpo-si (KR); Yongjae Kim, Seoul (KR); Youn Baek Lee, Yongin-si (KR); Jeonghun Kim, Hwaseong-si (KR); Se-Gon Roh, Suwon-si (KR); Minhyung Lee, Anyang-si (KR); Jongwon Lee, Uiwang-si (KR); Hyun Do Choi, Yongin-si (KR); Youngdo Kwon, Yongin-si (KR); ByungKwon Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 951 days.

(21) Appl. No.: 14/634,403

(22) Filed: Feb. 27, 2015

(65) Prior Publication Data

US 2015/0272811 A1     Oct. 1, 2015

(30) Foreign Application Priority Data

Mar. 28, 2014    (KR) .......................... 10-2014-0037081

(51) Int. Cl.
*A61H 1/02*      (2006.01)
*A61H 3/00*      (2006.01)
(Continued)

(52) U.S. Cl.
CPC ............. *A61H 3/00* (2013.01); *A61F 5/0123* (2013.01); *A61H 1/024* (2013.01); *B25J 9/0006* (2013.01);
(Continued)

(58) Field of Classification Search
CPC ...... A61H 1/02; A61H 1/0262; A61H 1/0237; A61H 1/024; A61H 3/00;
(Continued)

(56) References Cited

U.S. PATENT DOCUMENTS

| 5,020,790 | A | 6/1991 | Beard et al. |
| 7,998,096 | B1 * | 8/2011 | Skoog ..................... A61H 3/00 601/35 |

(Continued)

FOREIGN PATENT DOCUMENTS

| CN | 1136988 A | 12/1996 |
| CN | 2762777 Y | 3/2006 |

(Continued)

OTHER PUBLICATIONS

Extended European Search Report dated Jul. 28, 2015 for European Patent Application No. 15 16 1623.

(Continued)

*Primary Examiner* — Steven O Douglas
(74) *Attorney, Agent, or Firm* — Harness, Dickey & Pierce, P.L.C.

(57) ABSTRACT

In a joint assembly of a walking assistance robot that is capable of performing an operation with 3 degrees of freedom, similarly to a user's joint, a rolling motion and a sliding motion are simultaneously made, and a rotation center changes so that the joint assembly can make a similar motion to that of an actual knee joint of the user. Thus, when the user wears the walking assistance robot and walks, misalignment can be prevented from occurring in the knee joint.

21 Claims, 22 Drawing Sheets

(51) Int. Cl.
*B25J 9/00* (2006.01)
*B25J 17/00* (2006.01)
*A61F 5/01* (2006.01)

(52) U.S. Cl.
CPC ....... *B25J 17/00* (2013.01); *A61F 2005/0155* (2013.01); *A61H 1/0244* (2013.01); *A61H 2003/007* (2013.01); *A61H 2201/0107* (2013.01); *A61H 2201/1215* (2013.01); *A61H 2201/1246* (2013.01); *A61H 2201/1463* (2013.01); *A61H 2201/164* (2013.01); *A61H 2201/165* (2013.01); *A61H 2201/1628* (2013.01); *A61H 2201/5007* (2013.01); *A61H 2201/5061* (2013.01); *Y10T 74/20323* (2015.01)

(58) Field of Classification Search
CPC ........ A61H 2201/0157; A61H 2201/12; A61H 2201/14; A61H 2201/1436; A61H 2201/1481; A61H 2201/149; A61H 1/0244; A61H 2003/007; A61H 2201/0107; A61H 2201/1215; A61H 2201/1246; A61H 2201/1463; A61H 2201/1628; A61H 2201/164; A61H 2201/165; A61H 2201/5007; A61H 2201/5061; A61F 5/0123; B25J 9/0006; B25J 17/00; Y10T 74/20323
See application file for complete search history.

(56) References Cited

U.S. PATENT DOCUMENTS

| | | | |
|---|---|---|---|
| 9,682,006 B2 * | 6/2017 | Goldfarb | A61H 3/00 |
| 2006/0064047 A1 * | 3/2006 | Shimada | A61F 5/0102 |
| | | | 602/23 |
| 2010/0036302 A1 | 2/2010 | Shimada et al. | |
| 2010/0063424 A1 * | 3/2010 | Kudoh | A61H 3/008 |
| | | | 601/35 |
| 2011/0214524 A1 | 9/2011 | Jacobsen et al. | |
| 2014/0276265 A1 * | 9/2014 | Caires | A61H 3/00 |
| | | | 601/34 |
| 2015/0051527 A1 * | 2/2015 | Potter | A61F 5/0125 |
| | | | 602/16 |
| 2015/0374573 A1 * | 12/2015 | Horst | A61H 3/00 |
| | | | 602/16 |

FOREIGN PATENT DOCUMENTS

| | | |
|---|---|---|
| CN | 201064242 Y | 5/2008 |
| CN | 102551935 A | 7/2012 |
| JP | 2000237985 A | 9/2000 |
| JP | 2008200813 A | 9/2008 |
| JP | 2008260089 A | 10/2008 |
| JP | 2009153660 A | 7/2009 |
| JP | 2011098425 A | 5/2011 |
| JP | 4998623 B2 | 8/2012 |
| JP | 2013-070783 A | 4/2013 |
| JP | 2013-078526 A | 5/2013 |
| JP | 2013-150714 A | 8/2013 |
| KR | 10-2006-0039970 A | 5/2006 |
| KR | 20070057209 A | 6/2007 |
| KR | 20100082989 A | 7/2010 |
| KR | 10-2012-0082695 A | 7/2012 |
| WO | WO-2011129013 A1 | 10/2011 |

OTHER PUBLICATIONS

Stienen, A.H.A., "Self-Aligning Exoskeleton Axes Through Decoupling of Joint Rotations and Translations", Robotics, IEEE Transactions, vol. 25, Issue 3, IEEE, pp. 628-633.

Stienen, A.H.A., "Dampace: dynamic force-coordination trainer for the upper extremities", Rehabilitation Robitics, 2007, ICORR 2007. IEEE 10th International Conference, IEEE, pp. 820-826.

Office Action dated May 3, 2018 by the State Intellectual Property Office of P.R. China for CN Application No. 201510108843.8.

European Patent Office Communication Pursuant to Article 94(3) EPC dated Oct. 20, 2017 for EP Application No. 15 161 623.2.

European Patent Office Communication Pursuant to Article 94(3) EPC dated Feb. 23, 2018 for EP Application No. 15 161 623.2.

The Second Office Action dated Jan. 23, 2019 for CN Application No. 201510108843.8 by the National Intellectual Property Administration, PRC.

Japanese Office Action dated Jan. 29, 2019 for JP Application No. 2015-042287.

* cited by examiner

JOINT ASSEMBLY AND WALKING ASSISTANCE ROBOT

CROSS-REFERENCE TO RELATED APPLICATION

This application claims the benefit of Korean Patent Application No. P2014-37081, filed on Mar. 28, 2014 in the Korean Intellectual Property Office, the entire disclosure of which is incorporated herein by reference.

BACKGROUND

1. Field

Example embodiments relate to a joint assembly that assists with a user's motion and/or a walking assistance robot having the same.

2. Description of the Related Art

A walking assistance robot may be used as an assistance apparatus to assist a user with a weakened muscular strength and weight according to the field of usage or may be used as a strengthening apparatus that increases the user's muscular strength and supports a load of a heavy object to perform work thereon and/or transport the object having a large weight. However, conventionally, as the user moves, a rotation center of one or more joints of the walking assistance robot may not coincide with corresponding joints of the wearer which may result in misalignment of the limbs of the walking assistance robot.

SUMMARY

At least some example embodiments provide a joint assembly whose motion is similar to that of a user's joint and a walking assistance robot having the same.

Additional aspects of the example embodiments will be set forth in part in the description which follows and, in part, will be obvious from the description, or may be learned by practice thereof.

In accordance with some example embodiments, there is provided a joint assembly.

In some example embodiments, the joint assembly may include a first pulley that is rotatable around a first rotation shaft; a second pulley that is rotatable around a second rotation shaft; and a third pulley that is connected to the first pulley and the second pulley and rotatable around a third rotation shaft, wherein, if the first pulley is rotated around the first rotation shaft, a position of the second rotation shaft and a position of the third rotation shaft may be moved. If a driving force is transferred to the first pulley, a first frame connected to the first pulley or a second frame connected to the second pulley may be pivoted while a position of a rotation center of the first frame or the second frame changes. The first pulley, the second pulley, and the third pulley may be connected to one another using a wire.

A first gear may be formed on an outer circumferential surface of the first pulley, and a second gear may be formed on an outer circumferential surface of the second pulley, and a third gear may be formed on an outer circumferential surface of the third pulley.

A first auxiliary gear that is engaged with the first gear and the third gear may be disposed between the first pulley and the third pulley, and a second auxiliary gear that is engaged with the third gear and the second gear may be disposed between the third pulley and the second pulley.

A wire connected to a driving source may be connected to the first pulley.

A driving pulley may be connected to the first pulley, and the wire connected to the driving source may be connected to the driving pulley, and a driving force transferred to the driving pulley may be transferred to the first pulley.

The first pulley and the driving pulley may be formed integrally.

The joint assembly may further include: a first main link having one side on which the first pulley is mounted and the other side to which the first frame is connected; and a second main link having one side on which the second pulley is mounted and the other side to which the second frame is connected.

The joint assembly may further include: a first auxiliary link that connects the first main link and the third pulley; and a second auxiliary link that connects the third pulley and the second main link.

The joint assembly may further include: a first rotation shaft that passes through one side of the first auxiliary link, the first main link, and the first pulley; a second rotation shaft that passes through one side of the second auxiliary link, the second main link, and the second pulley; and a third rotation shaft that passes through the other side of the first auxiliary link, the third pulley, and the other side of the second auxiliary link.

A lower surface of the first main link may have a non-uniform height, and an upper surface of the second main link may be disposed to correspond to a shape of the lower surface of the first main link and may support the first main link when the first frame and the second frame extend in a straight line.

A first guide portion may be formed at one side of the first main link, and a second guide portion may be formed at one side of the second main link so that, when the first frame or the second frame is pivoted, the first guide portion is supported by the second guide portion.

A buffer member formed of a material including silicon or rubber may be mounted on a contact surface on which the first main link and the second main link contact each other.

The first main link and the second main link may be connected to each other using a link unit that is pivotally disposed, and when the first frame and the second frame extend in a straight line, the link unit may be disposed between the first main link and the second main link.

The first main link and the second main link may be connected to each other using an elastic unit that is pivotally disposed, and if the first frame and the second frame extend in a straight line, the elastic unit may be disposed between the first main link and the second main link.

Other example embodiments relate to a walking assistance robot that is mounted on a user's body and assists with the user's walking.

In some example embodiments, the walking assistance robot includes a first frame mounted on the user's thigh; and a second frame mounted on the user's calf and connected to the first frame using a knee joint assembly, wherein the knee joint assembly may include: a first main link which is mounted on the first frame and on which a first pulley to which a driving force is transferred, is mounted; a second main link which is mounted on the second frame and on which a second pulley is mounted; and a third pulley connected to the first pulley and the second pulley, and if the driving force is transferred to the first pulley and the first pulley is rotated by the driving force in one direction, the second pulley and the third pulley are rotated in one direction, and a position of a rotation center of the third pulley and a position of a rotation center of the second pulley are moved.

A load applied to the first frame or the second frame can be supported when the first main link is supported by the second main link.

The first main link and the second main link may be connected to each other using a link unit, and the link unit may include: a first support link having one side that is pivotally mounted on the first main link; and a second support link having one side that is pivotally mounted on the second main link and the other side that is pivotally mounted on the other side of the first support link.

If the first frame and the second frame extend in a straight line, the first support link and the second support link may be folded and disposed between the first main link and the second main link and may support a load applied to the knee joint assembly.

The first main link and the second main link may be connected to each other using an elastic unit, and the elastic unit may be disposed between the first main link and the second main link and may support a load applied to the knee joint assembly.

The first main link and the third pulley may be connected to each other using a first auxiliary link, and the second main link and the third pulley may be connected to each other using a second auxiliary link.

If the second frame is pivoted with respect to the first frame, an angle formed between the first auxiliary link and the second auxiliary link at the third pulley may change.

The first pulley may be connected to a driving pulley using a wire, and at least one of one end and the other end of the wire that connects the first pulley and the driving pulley may be connected to a driving source.

The first pulley, the second pulley, and the third pulley may be connected to one another using a wire, and the first pulley, the wire, the second pulley, and the third pulley may be together rotated by a driving force transferred to the first pulley.

Gears may be formed on outer circumferential surfaces of the first pulley, the second pulley, and the third pulley, respectively, and the first pulley, the second pulley, and the third pulley may be connected to one another using auxiliary gears engaged with the gears.

Other example embodiments relate to a walking assistance robot mounted on a user's body so as to assist with the user's walking.

In some example embodiments, the walking assistance robot includes a first frame mounted on the user's thigh; a second frame mounted on the user's calf; and a knee joint assembly that pivotally connects the first frame and the second frame and supports a load, wherein the knee joint assembly may include: a first main link that is pivotally connected to the first frame; a second main link that is pivotally connected to the second frame; a first auxiliary link having one side pivotally connected to the first main link using a first rotation shaft; and a second auxiliary link having one side pivotally connected to the second main link using a second rotation shaft and the second auxiliary link being pivotally connected to the other side of the first auxiliary link using a third rotation shaft, and if a driving force is transferred to the one side of the first auxiliary link, the third rotation shaft and the second rotation shaft are moved.

An angle between the first auxiliary link and the second auxiliary link at the third rotation shaft may change due to the driving force transferred to the one side of the first auxiliary link so that the second frame is pivoted with respect to the first frame.

The walking assistance robot may further include: a first pulley on which the first rotation shaft is mounted and to which the driving force is transferred; a second pulley on which the second rotation shaft is mounted; and a third pulley on which the third rotation shaft is mounted.

The first pulley, the second pulley, and the third pulley may be connected to one another using one wire.

The third pulley may be simultaneously rotated around the first rotation shaft and rotated around the third rotation shaft, and the second pulley may be simultaneously rotated around the third rotation shaft and rotated around the second rotation shaft.

At least some example embodiments may relate to a joint assembly.

In some example embodiments, the joint assembly may be configured to connect a first frame and a second frame that are configured to respectively mount on upper and lower portions of a leg wearer.

In some example embodiments, the joint assembly may include a first pulley configured to rotate around a first shaft formed in the first frame and a first end of a first auxiliary link; a second pulley configured to rotate around a second shaft formed in a second end of the first auxiliary link and a first end of a second auxiliary link in response to a rotation of the first pulley; a third pulley configured rotate around a third shaft formed in the second frame and a second end of the second auxiliary link in response to the rotation of the first pulley such that a position of the second shaft and the third shaft changes relative to the first shaft.

In some example embodiments, the joint assembly includes a wire configured to connect the first pulley, the second pulley, and the third pulley; and a driver configured to pull the wire such that the first, second and third pulleys rotate in a same direction while a rotational center of the second shaft and the third shaft move relative to the first pulley.

In some example embodiments, the joint assembly includes a processor configured to instruct the driver to pull the wire with an amount of tension determined based on one or more of a weight of a wearer of the joint assembly and a current phase of a walking cycle of the wearer.

In some example embodiments, the joint assembly is configured to simultaneously roll and slide such that the first frame and second frame maintain alignment with the upper and lower portions of the leg of the wearer respectively when the joint assembly bends.

BRIEF DESCRIPTION OF THE DRAWINGS

These and/or other aspects of the example embodiments will become apparent and more readily appreciated from the following description of some of the example embodiments, taken in conjunction with the accompanying drawings of which.

DETAILED DESCRIPTION

Figure 1:
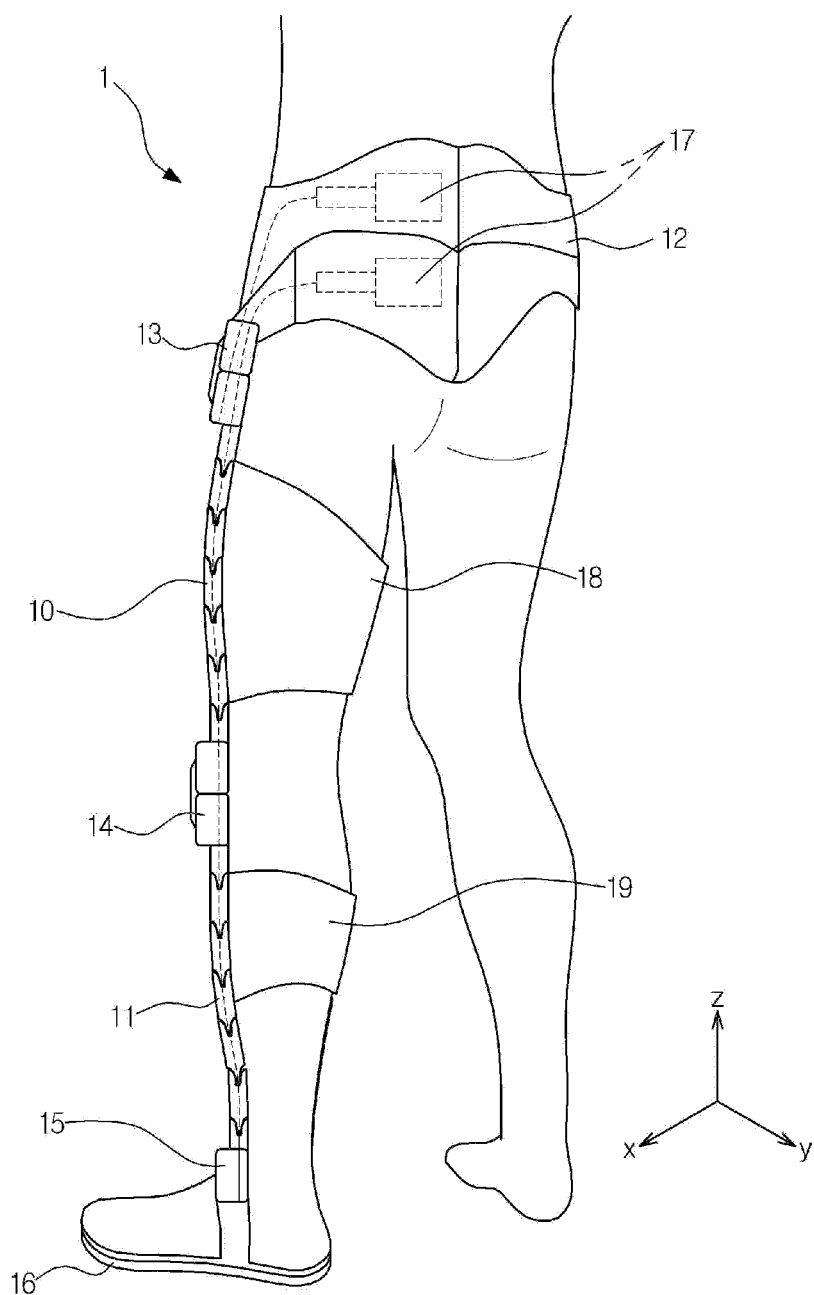
FIG. 1 is a conceptual view of a walking assistance robot according to some example embodiments.

Reference will now be made in detail to the example embodiments, some examples of which are illustrated in the accompanying drawings, wherein like reference numerals refer to like elements throughout.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 is a conceptual view of a walking assistance robot according to some example embodiments.

Referring to FIG. 1, a walking assistance robot 1 includes frames 10 and 11 that extend along a lengthwise direction of a user's leg. The frames 10 and 11 may include a first frame 10 fixed to the user's thigh and a second frame 11 fixed to the user's calf. The walking assistance robot 1 may further include a foot structure 16 mounted on the user's foot and a waist fixing unit 12. The first frame 10 and the waist fixing unit 12 may be pivotally connected to each other using a hip joint 13, and the first frame 10 and the second frame 11 may be pivotally connected to each other using a knee joint 14, and the second frame 11 and the foot structure 16 may be pivotally connected to each other using an ankle joint 15.

The walking assistance robot 1 may further include a driving source 17 and fixing units 18 and 19. The driving source 17 may provide a driving force to one or more of the hip joint 13 and the knee joint 14, and the fixing units 18 and 19 may cause the frames 10 and 11 to be mounted on the user's body.

For example, a first fixing unit 18 may be connected to the first frame 10 and may be fixed to the user's thigh. Similarly, a second fixing unit 19 may be connected to the second frame 11 and may be fixed to the user's calf. The first fixing unit 18 and the second fixing unit 19 may be formed of a fastener and may be adjustable such that a size of the fixing units 18 and 19 can accommodate the size of the user's leg.

The waist fixing unit 12 may be formed of a flexible strap so as to be adjusted to be suitable for the user's waist size. For example, the waist fixing unit 12 may be a hook-end-loop fixing unit formed of a hook-and-loop fastener or a strap including a fixing portion, such as a ratchet buckle or catch.

The hip joint 13 may be provided to have 3 degrees of freedom so that the first frame 10 connected to the hip joint 13 may be pivoted around an x-axis, a y-axis, and a z-axis. For example, the first frame 10 may be pivoted around the x-axis using the hip joint 13 to which the driving force is transmitted from the driving source 17. The first frame 10 may also be pivoted around the y-axis using a hinge unit. The first frame 10 or the hip joint 13 to which the first frame 10 is connected, may be provided to be slidable along the waist fixing unit 12 so that the first frame 10 may be pivoted around the z-axis.

The ankle joint 15 may also have 3 degrees of freedom such that the second frame 11 or the foot structure 16 may be provided to be pivoted around the x-axis, the y-axis, and the z-axis based on the ankle joint 15.

The foot structure 16 may be fixed to the user's foot. A sensor may be provided on a bottom surface of the foot structure 16. The sensor may detect a change in a load of the user who wears the walking assistance robot 1, and may transmit information regarding the detected change in the user's load to a controller (not shown). The controller (not shown) may control a motion of the hip joint 13 or the knee joint 14 using the information detected by the sensor.

Hereinafter, for the sake of brevity a single first frame 10, knee joint 14 and second frame 11 will be described, but the corresponding descriptions may be equally applied to pairs of the respective structure units, for example, left and right versions thereof.

Figure 2A:
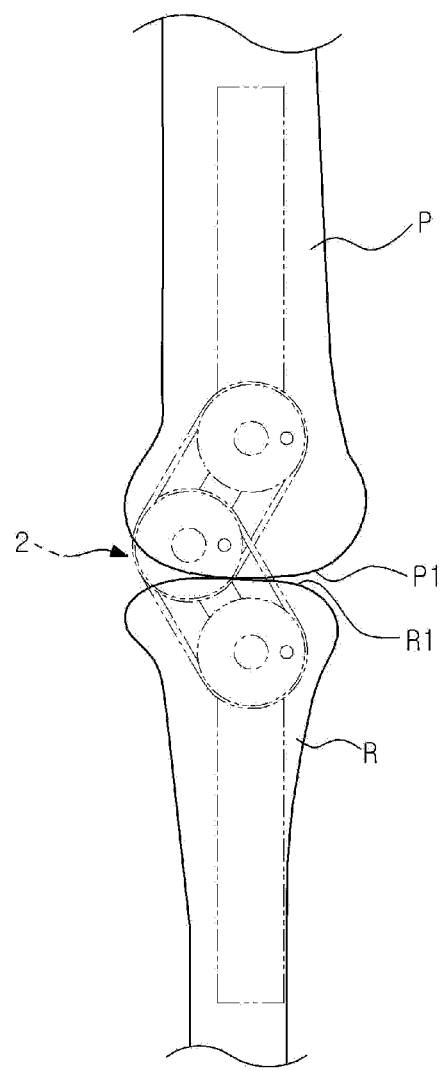
FIGS. 2A and 2B are views for describing a motion of a user's knee joint on which the walking assistance robot illustrated in FIG. 1 is mounted.
Figure 2B:
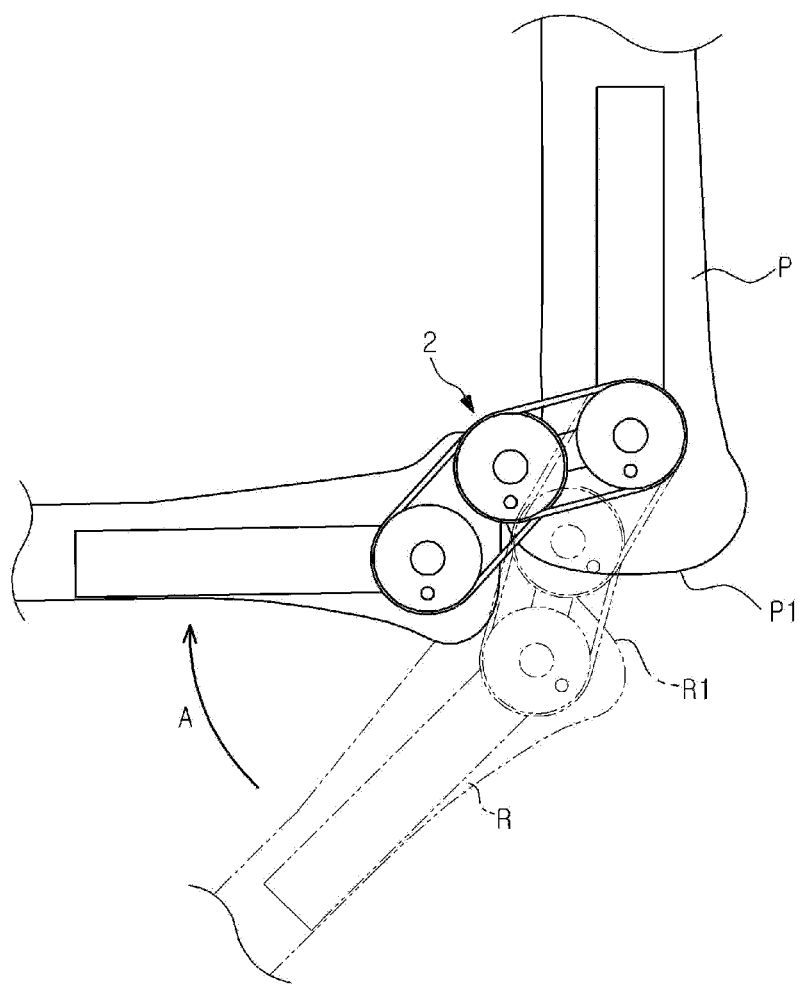

FIGS. 2A and 2B are views for describing a motion of a user's knee joint on which the walking assistance robot illustrated in FIG. 1 is mounted.

Referring to FIGS. 1, 2A and 2B, the knee joint 14 of the walking assistance robot 1 may be move with the motion of the user's knee joint. However, the user's knee joint may roll and slide simultaneously while the user's knee is bent or stretched. Thus, when the user's thigh or calf is pivoted around the knee joint, a rotation center of the user's knee joint may be moved.

For example, a calf bone R may make a rolling motion around a thigh bone P in one direction A. An end surface R1 of the calf bone R may slide along an end surface P1 of the thigh bone P simultaneously when the calf bone R makes the rolling motion in one direction A. Thus, when the calf bone R is rolled, the end surface R1 of the calf bone R slides along the end surface P1 of the thigh bone P so that a rotation center of the rolling motion of the calf bone R may change.

If the user's knee joint is pivoted simultaneously by the rolling and sliding motions, if the knee joint of a walking assistance robot is provided to be pivoted around one rotation shaft, the rotation center of the user's knee joint and the rotation center of the knee joint of the walking assistance robot may not coincide. If the rotation center of the user's knee joint and the rotation center of the knee joint of the walking assistance robot do not coincide, misalignment may occur in the knee joint of the walking assistance robot. When misalignment occurs in the knee joint of the walking assistance robot, the user's body may be tilted by the frame included in the walking assistance robot or the user may be uncomfortable when he/she sits down or stands up while performing a walking motion using the walking assistance robot.

In contrast, the knee joint of the walking assistance robot 1 according to some example embodiments may make a motion similar to that of the actual knee joint of the user. Therefore, the walking assistance robot 1 may reduce the discomfort or resistance felt by the user when the user walks.

Figure 3:
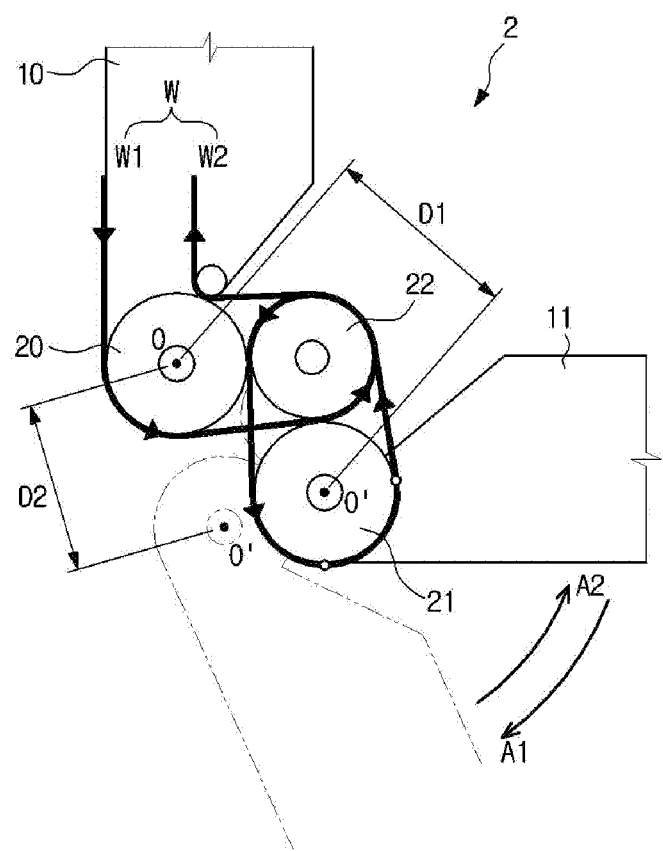
FIG. 3 is a conceptual view of a knee joint of a walking assistance robot according to some example embodiments.

FIG. 3 is a conceptual view of a knee joint of a walking assistance robot according to some example embodiments.

Referring to FIGS. 1 and 3, the knee joint 14 included in the walking assistance robot 1 may include a joint assembly 2. The joint assembly may include a first pulley 20, a second pulley 21, and a third pulley 22.

The first pulley 20 may be mounted on an end of the first frame 10 that faces the second frame 11. Similarly, the second pulley 21 may be mounted on an end of the second frame 11 that faces the first frame 10. The third pulley 22 may be connected to the first pulley 20 and the second pulley 21 using a wire W and may be moved according to a motion of the first frame 10 or the second frame 11.

In some example embodiments, a wire W may be wound around the first pulley 20 in a direction of arrow, may extend toward the third pulley 22, may be at least once wound around the entire outer circumferential surface of the third pulley 22, may extend toward the second pulley 21, may be wound around an outer circumferential surface of the second pulley 21, may pass the third pulley 22, and may extend up to the first pulley 20. Ends W1 and W2 of the wire W may be connected to the driving source 17 (see FIG. 1).

The wire W may pivot the first frame 10 and/or the second frame 11 by transferring the driving force of the driving source 17 to the first pulley 20, the second pulley 21, and/or the third pulley 22 and by rotating the first pulley 20, the second pulley 21, and/or the third pulley 22. If the driving source 17 pulls a first end W1 of the wire W, the second pulley 21 may be rolled (rotated) and may pivot the second frame 11 in a clockwise direction A1. The third pulley 22 may slide along an outer circumferential surface of the first pulley 20 and may be rolled in the clockwise direction A1. As a result, the second pulley 21 may be rolled in the clockwise direction A1 while being moved along an outer circumferential surface of the third pulley 22.

In this way, the second pulley 21 and the third pulley 22 make sliding and rolling motions using the wire W so that the sliding and rolling motions of the second frame 11 on which the second pulley 21 is mounted, may be simultaneously implemented. For example, a position of the rotation center of the third pulley 22 may be moved in the clockwise direction A1 along the circumference of the first pulley 20, and a position of the rotation center of the second pulley 21 may be moved in the clockwise direction A1 along the circumference of the third pulley 22. By using the joint assembly 2, the second frame 11 may be pivoted with respect to the first frame 10 in the clockwise direction A1, similarly to a motion of the actual knee joint of the user when the user stretches the knee. A distance D2 between a central point O of the first pulley 20 and a central point O' of the second pulley 21 after the second frame 11 is pivoted in the clockwise direction A1, is smaller than a distance D1 between the central point O of the first pulley 20 and the central point O' of the second pulley 21 before the first frame 10 or the second frame 11 is pivoted.

If the driving source 17 pulls the other end W2 of the wire W, the second pulley 21 may pivot the second frame 11 in a counterclockwise direction A2 while making a rolling motion. The third pulley 22 may slide along the circumference of the first pulley 20 and may be rolled in the counterclockwise direction A2 so that the rotation center of the third pulley 22 may be moved in the counterclockwise direction A2 along the circumference of the first pulley 20. As a result, the second pulley 21 may be moved along the outer circumferential surface of the third pulley 22 and may be rolled in the counterclockwise direction A2 so that the rotation center of the second pulley 21 may be moved in the counterclockwise direction A2 along the circumference of the third pulley 22. In this way, the second pulley 21 and the third pulley 22 may make sliding and rolling motions using the wire W so that the second frame 11 on which the second pulley 21 is mounted, may be pivoted in the counterclockwise direction A2, similarly to the knee joint of the user when the user bends the knee. The distance D1 between the central point O of the first pulley 20 and the central point O' of the second pulley 21 after the second frame 11 is pivoted in the counterclockwise direction A2, is greater than the distance D2 between the central point O of the first pulley 20 and the central point O' of the second pulley 21 before the first frame 10 or the second frame 11 is pivoted.

The knee joint 14 of the walking assistance robot 1 may include the joint assembly 2 having a structure in which three pulleys 20, 21, and 22 are connected to one another using the wire W. The joint assembly 2 may cause the first frame 10 or the second frame 11 to simultaneously make sliding and rolling motions so that the knee joint 14 of the walking assistance robot 1 may be pivoted, similarly to the user's knee joint.

For convenience, in FIG. 3, the second frame 11 is moved with 2 degrees of freedom with respect to the first frame 10 to have sliding and rolling motions. In other example embodiments, the first frame 10 may make sliding and rolling motions with 2 degrees of freedom with respect to the second frame 11.

Figure 4:
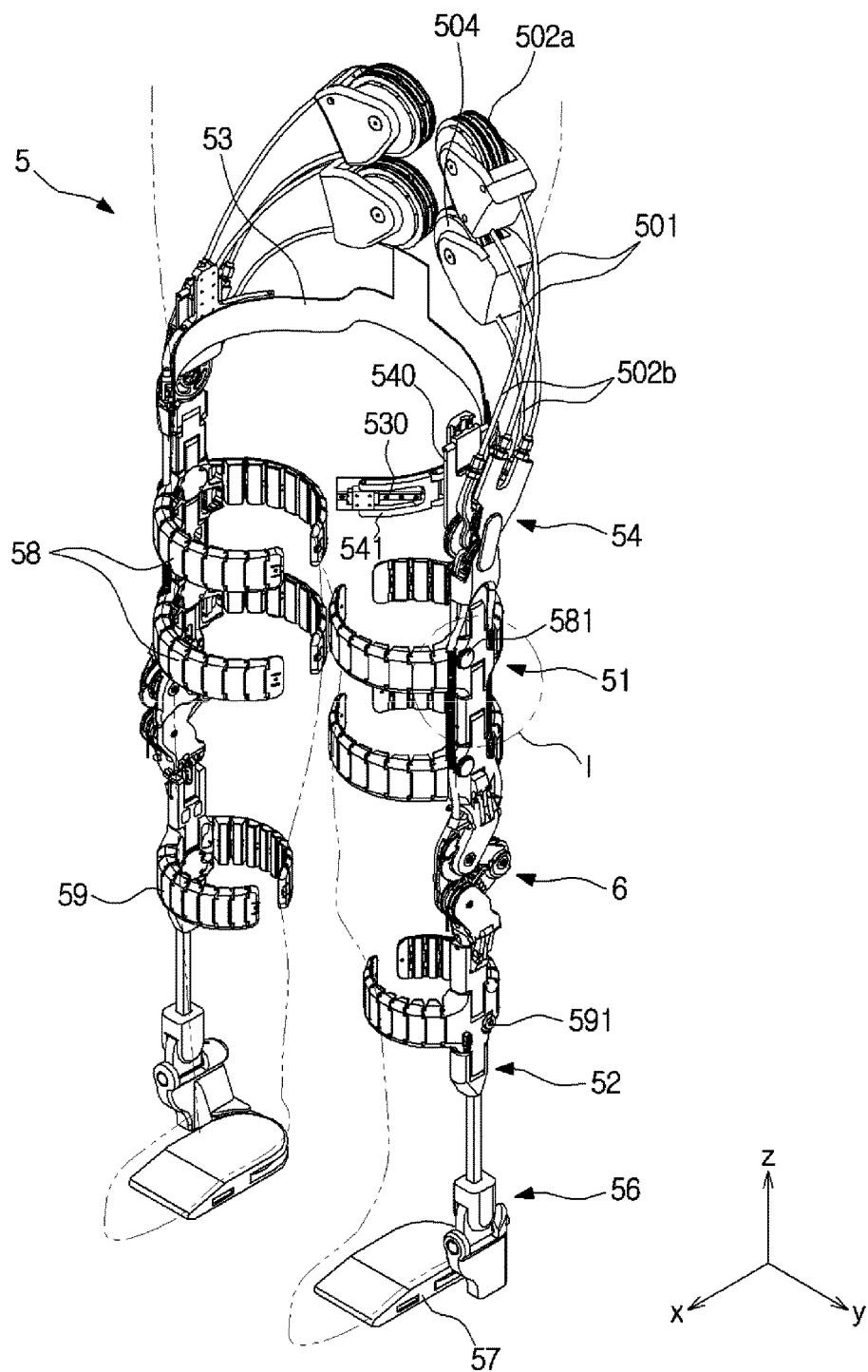
FIG. 4 is a view of a walking assistance robot according to some example embodiments.

FIG. 4 is a view of a walking assistance robot according to other example embodiments.

Referring to FIG. 4, a walking assistance robot 5 according to other example embodiments may include frames 51 and 52 that extend in the lengthwise direction of the user's leg and support the user's load. The frames 51 and 52 may include a first frame 51 that supports the user's thigh and a second frame 52 that supports the user's calf. The first frame 51 may be pivotally connected to a waist fixing unit 53 fixed to the user's waist using a hip joint 54. The first frame 51 and the second frame 52 may be pivotally connected to each other using a knee joint 6, and a foot structure 57 fixed to the user's foot may be connected to the second frame 52. The second frame 52 and the foot structure 57 may be pivotally connected to each other using an ankle joint 56.

The walking assistance robot 5 may further include a driving source that provides a driving force to the hip joint 54 and the knee joint 6 and a controller that controls an operation of the walking assistance robot 5. A sensor may be disposed at the foot structure 57, and information regarding the user's motion detected by the sensor may be transmitted to the controller. The controller may control the motion of the hip joint 54 or the knee joint 6 using the transmitted information.

The first frame 51 may be pivoted by reducing or extending a wire 501. The wire 501 may be wound on a pulley 502 connected to the driving source and may be connected to the first frame 51 using the hip joint 54. For example, if the driving source rotates the pulley 502 so as to cause the wire 501 to be wound around the pulley 502, the first frame 51 may be pivoted around the y-axis. If the driving source rotates the pulley 502 so as to cause the wire 501 to be unwound from the pulley 502, the first frame 51 may be pivoted around the y-axis in an opposite direction to a direction of the previous case.

The hip joint 54 and the waist fixing unit 53 may be connected to each other using a hinge unit 540 and may be rotated around the x-axis. If the hip joint 54 is rotated by the hinge unit 540, the first frame 51 connected to the hip joint 54 may be pivoted around the x-axis.

A sliding portion 541 may be disposed on a rear surface of the hinge unit 540, and a rail portion 530 may be disposed on the waist fixing unit 53. The rail portion 530 may extend in a direction of the user's waist, and the sliding portion 541 may slide along the rail portion 530 according to the user's motion. The sliding portion 541 slides along the rail portion 530 so that the hip joint 54 and the first frame 51 connected to the hinge unit 540 may be pivoted around the z-axis.

In this way, the first frame 51 may be pivoted to have 3 degrees of freedom using the hip joint 54, the hinge unit 540, and the rail portion 530. The movement in one of the three degrees of freedom in which the first frame 51 is pivoted around the hip joint 54 using the wire 501, may be performed using power, and movement in the remaining two degrees of freedom may be performed manually by the user's motion without using power.

The second frame 52 may be connected to the first frame 51 to have 3 degrees of freedom (DOF) with respect to the first frame 51 using the knee joint 6. The second frame 52 may be pivoted around the y-axis using the knee joint 6. The second frame 52 may be moved on a plane formed by the x-axis and the z-axis, to have redundancy of 2 degrees of freedom. The redundancy of 2 degrees of freedom may be secured by an auxiliary link 65 that will be described later.

When the second frame 52 is pivoted around the y-axis with respect to the first frame 51, the second frame 52 may be moved on the plane formed by the x-axis and the z-axis, by rolling and sliding motions of the knee joint 6. Although an operation with 1 degree of freedom in which the second frame 52 is pivoted around the y-axis, is performed using power, an operation with 2 degrees of freedom performed by the rolling and sliding motions of the knee joint 6 may be performed according to the user's motion without using power. By using the redundancy of 2 degrees of freedom, the knee joint 6 of the walking assistance robot 5 may make a similar motion to that of the actual knee joint of the user.

A DOF may mean the number of independent motions of a mechanism, or the number of independent parameters that are required to specify an independent motion at a relative position with respect to links. For example, an object that is in a 3-Dimensional (3D) space composed of x-, y-, and z-axes has one or more DOF of 3 DOF (positions on the respective axes) to specify a spatial position of the object, and 3 DOF (rotation angles with respect to the respective axes) to specify a spatial orientation of the object. If a certain object is movable on the individual axes and rotatable with respect to the individual axes, the object may be understood to have 6 DOF.

The second frame 52 may be pivoted by reducing or extending a wire 503. The wire 503 may be wound around a pulley 504 connected to the driving source and may be connected to the second frame 52 using the knee joint 6. A pivoting motion of the knee joint 6 will be described later.

The foot structure 57 may be pivoted with 3 degrees of freedom with respect to the second frame 52. The foot structure 57 and the second frame 52 may be pivotally connected to each other using the ankle joint 56, and the foot structure 57 or the second frame 52 may be pivoted around the ankle joint 56 according to the user's motion without using power.

A first fixing unit 58 may be connected to the first frame 51 so as to surround the user's thigh and may cause the first frame 51 to be mounted on the user's thigh. Similarly, a second fixing unit 59 may be connected to the second frame 52 so as to surround the user's calf and may cause the second frame 52 to be mounted on the user's calf. The first fixing unit 58 and/or the second fixing unit 59 may be configured of a plurality of links connected to one another. For example, the plurality of links may be connected to one another using a cable (not shown). The plurality of links may be formed of a rigid material.

Manipulation units 581 and 591 may be disposed at the first fixing unit 58 and the second fixing unit 59, respectively, so as to adjust the length of the cable. The manipulation units 581 and 591 may be buttons or dials through which the user may extend or reduce the cable (not shown). If the cable is reduced, the first fixing unit 58 or the second fixing unit 59 may tighten around the user's leg. Contrary to this, if the cable is extended, the first fixing unit 58 or the second fixing unit 59 may separate from the user's leg.

The user may extend or reduce the cable by manipulating the manipulation units 581 and 591 so as to tighten the first fixing unit 58 and the second fixing unit 59 to the user's leg or to separate the first fixing unit 58 and the second fixing unit 59 from the user's leg and may adjust pressure used to tighten the user's leg using the first fixing unit 58 and the second fixing unit 59, at an appropriate level.

Figure 5:
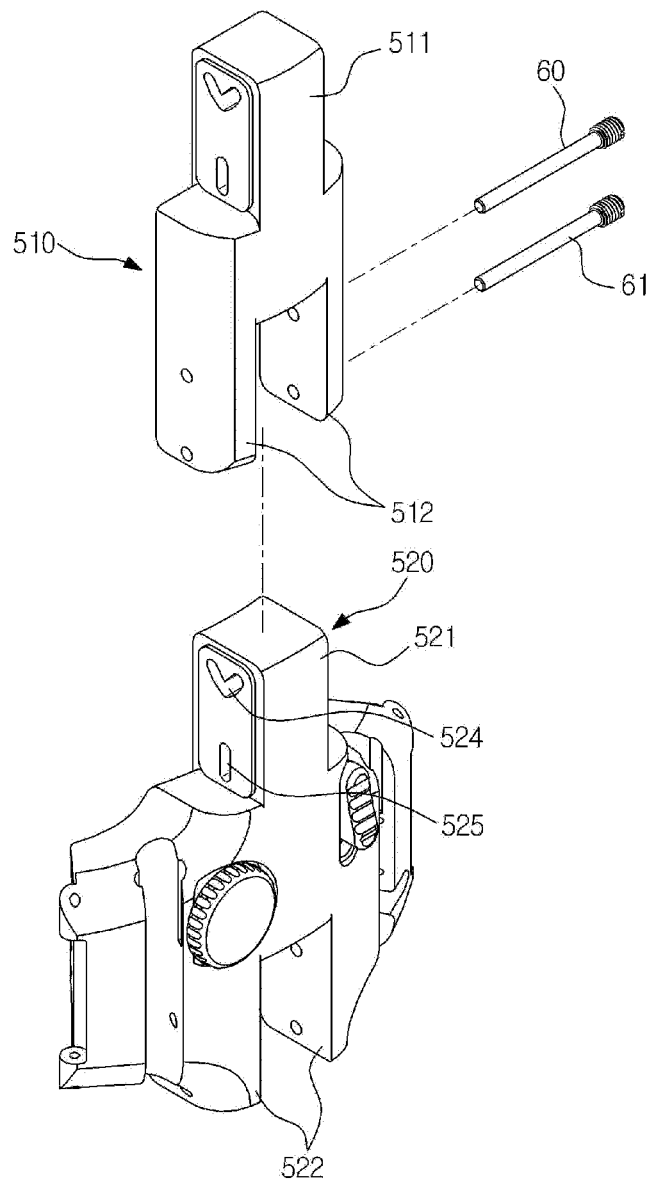
FIG. 5 is an exploded perspective view of portion I of FIG. 4.

FIG. 5 is an exploded perspective view of portion I of FIG. 4.

Referring to FIG. 5, the frames 51 and 52 of the walking assistance robot 5 may be disposed to extend in the lengthwise direction of the user's leg and may be configured of a plurality of links connected to one another. The first frame 51 and/or the second frame 52 may be configured of the plurality of links that are pivotally connected to one another, may be flexibly bent according to a curve of the user's body, and may stably support the user's load. The plurality of links may be formed of a rigid material.

A first link 510 and a second link 520 that constitute the first frame 51 and/or the second frame 52 may be pivotally connected to each other. The first link 510 may include a first coupling portion 511 and a second coupling portion 512. The first coupling portion 511 may protrude from one side of the first link 510. The second coupling portion 512 may protrude from the other side of the first link 510 that faces the one side at which the first coupling portion 511 is formed. The second link 520 may include a first coupling portion 521 and a second coupling portion 522 similarly to the first link 510. The first coupling portion 521 may protrude from one side of the second link 520. The second coupling portion 522 may protrude from the other side of the second link 520 that faces the one side at which the first coupling portion 521 is formed.

The first coupling portion 521 of the second link 520 may include a first slot 524 having a shape of a downwardly-concave curve and a second slot 525 having a shape of a straight line that extends in a vertical direction. The first link 510 and the second link 520 may be pivotally connected to each other using a first pin 60 that passes through the first slot 524 and a second pin 61 that passes through the second slot 525. Therefore, when the second link 520 is pivoted with respect to the first link 510, the first pin 60 may be guided by the first slot 524, and the second pin 61 may be guided by the second slot 525. The first pin 60 may be supported by an inner sidewall of the first slot 524, and the second pin 61 may be supported by an inner sidewall of the second slot 525.

Through the above structure, when the user wears the walking assistance robot 5, the frame may be flexibly bent according to the curve of the user's body and may be in relatively close contact with the user's body, and the user's load may be more stably supported by the frame.

Figure 6A:
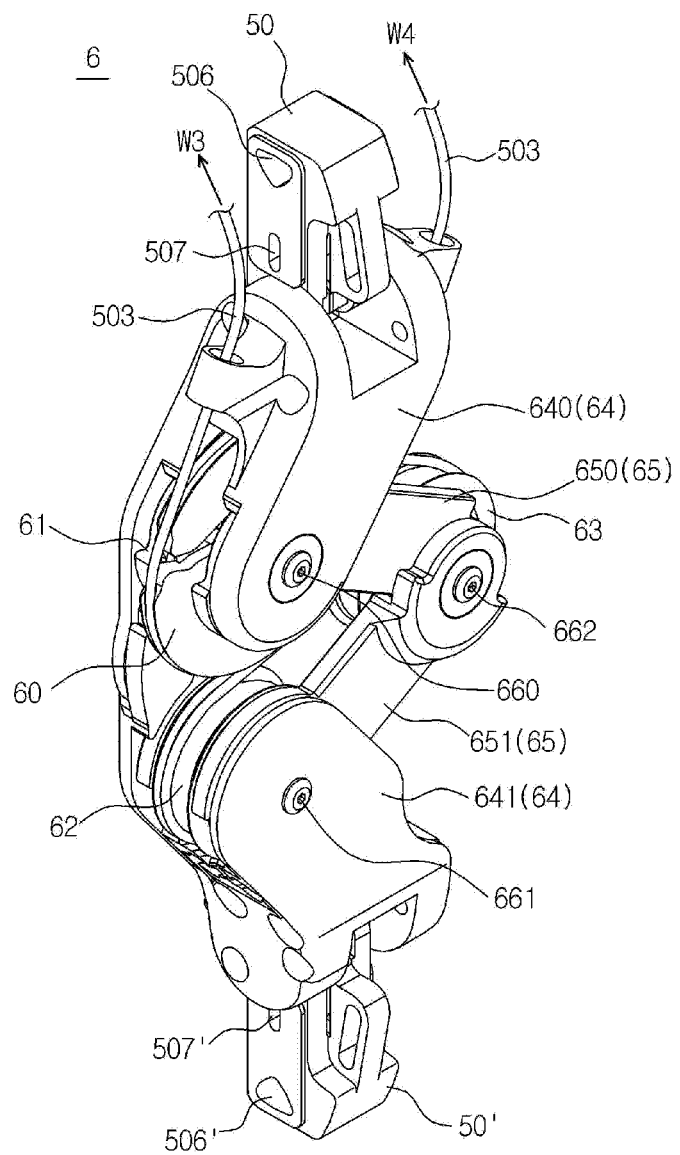
FIGS. 6A and 6B are views for describing a motion of the knee joint included in the walking assistance robot illustrated in FIG. 4.
Figure 6B:
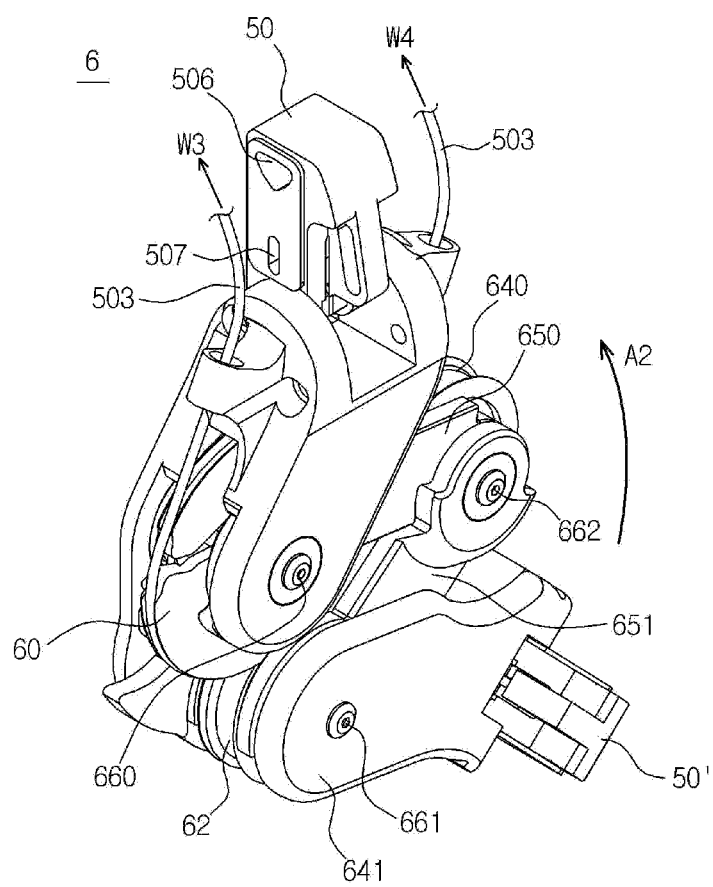
Figure 7:
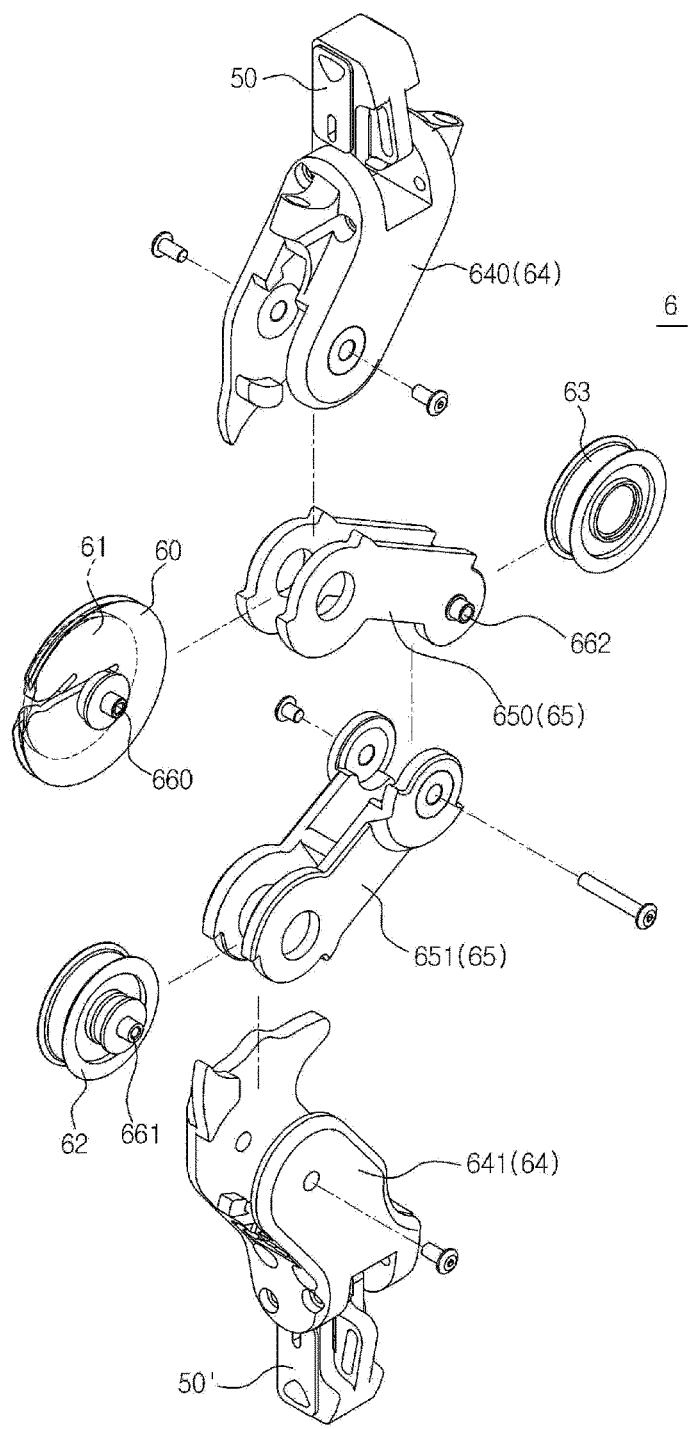
FIG. 7 is an exploded perspective view of the knee joint included in the walking assistance robot of FIG. 4.
Figure 8A:
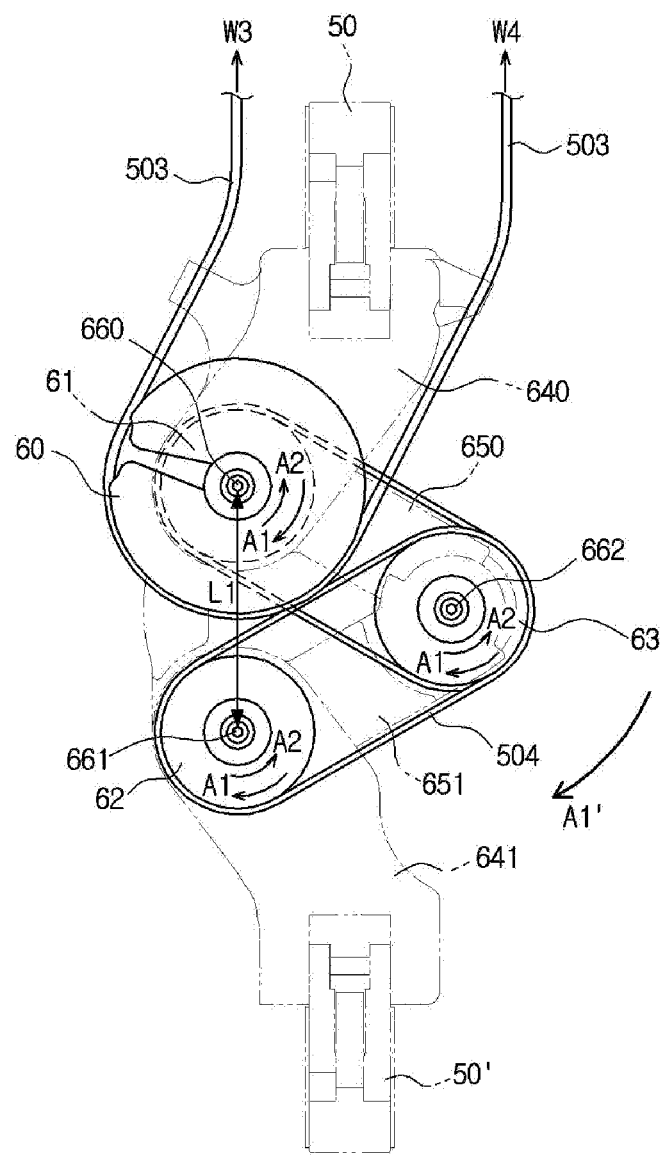
FIGS. 8A and 8B are views for describing a motion of a knee joint and a driving force transferring structure according to some example embodiments.
Figure 8B:
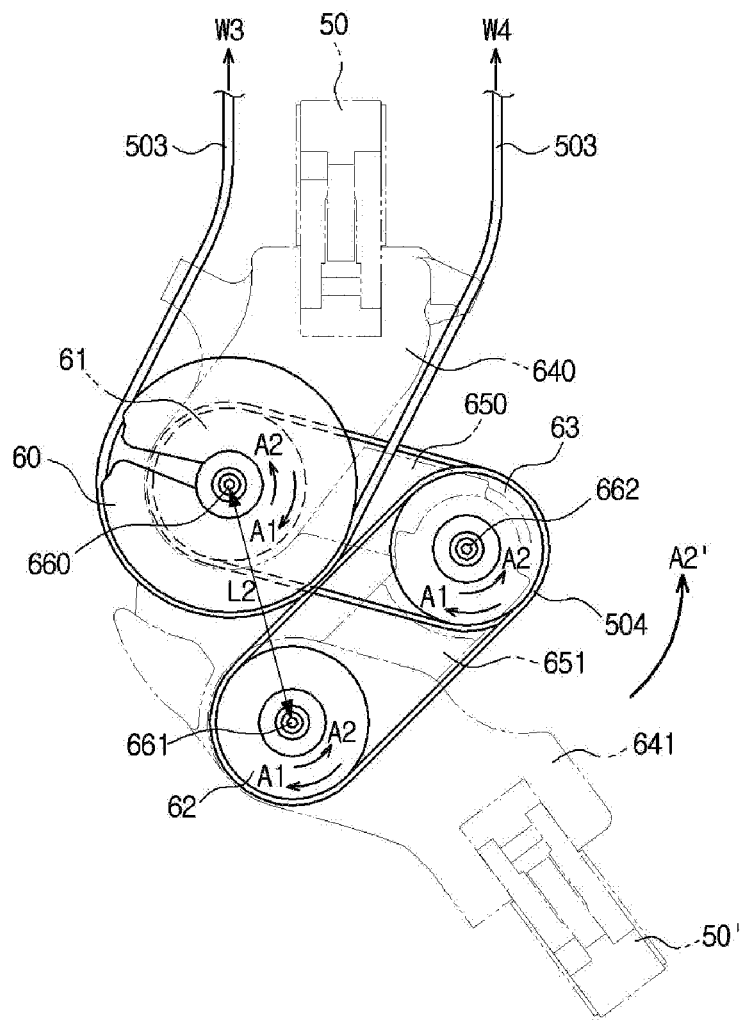

FIGS. 6A and 6B are views for describing a motion of the knee joint included in the walking assistance robot illustrated in FIG. 4, FIG. 7 is an exploded perspective view of the knee joint included in the walking assistance robot of FIG. 4, and FIGS. 8A and 8B are views for describing a motion of a knee joint and a driving force transferring structure according to some example embodiments.

Referring to FIGS. 6A through 8B, the knee joint 6 of the walking assistance robot 5 may include a joint assembly including a plurality of links that are pivotally connected to one another. The knee joint 6 of the walking assistance robot 5 may be pivoted by simultaneously making sliding and rolling motions, similarly to an actual knee joint of the user who wears the walking assistance robot 5.

The knee joint 6 may include a main link 64 and an auxiliary link 65. The main link 64 may include a first main link 640 that is pivotally connected to the first frame 51 and a second main link 641 that is pivotally connected to the second frame 52.

The first main link 640 may be connected to a bottom end of the first frame 51, and the second main link 641 may be connected to a top end of the second frame 52. For example, an upper portion or a lower portion of the main link 64 may be connected to the first frame 51 or the second frame 52 using connection links 50 and 50'. The connection links 50 and 50' may include a first connection link 50 and a second connection link 50'. The connection links 50 and 50' may be pivotally connected to the upper portion and the lower portion of the main link 64, respectively.

The connection links 50 and 50' may include first slots 506 and 506' having a shape of a curve that is concave in one direction and second slots 507 and 507' having a shape of a straight line that extends in the vertical direction, similarly to coupling of the plurality of links that constitute the first frame 51 or the second frame 52. The connection links 50 and 50' may be pivotally connected to another link adjacent to the connection links 50 and 50' using a first pin (not shown) that passes through the first slots 506 and 506' and a second pin (not shown) that passes through the second slots 507 and 507'.

The knee joint 6 may include a driving pulley 60, a first pulley 61, a second pulley 62, and a third pulley 63. The driving pulley 60 and the first pulley 61 may be provided as a single body. For example, the driving pulley 60 and the first pulley 61 may be provided as a double pulley and, thus, the driving pulley 60 and the first pulley 61 may operate together.

The first pulley 61 may be mounted on the first main link 640, and the second pulley 62 may be mounted on the second main link 641. The third pulley 63 may be connected to the first pulley 61 and the second pulley 62 using a wire that will be described later. The driving pulley 60 may be connected to the driving source using the first wire 503. The first pulley 61, the second pulley 62, and the third pulley 63 may be connected to one another using a second wire 504. The second wire 504 may be provided in the form of a loop. A driving force generated by the driving source may be transferred to the driving pulley 60 by the first wire 503. The driving force may also be transferred to the first pulley 61 formed integrally with the driving pulley 60. The driving force transferred to the first pulley 61 may be transferred to the second pulley 62 and the third pulley 63 using the second wire 504. Although the first wire 503 and the second wire 504 are illustrated a separate wires, in some example embodiments the first wire 503 and the second wire 504 may be a single wire. For example, a single wire may be at least once wound around the driving pulley 60, the first pulley 61, the second pulley 62, and the third pulley 63 respectively, and one end and the other end of the one wire may be connected to the driving source. The driving force may be transferred to the first pulley 61, the second pulley 62, and the third pulley 63 using the one wire.

Hereinafter, an example embodiment in which the first wire 503 that connects the driving source and the driving pulley 60 and the second wire 504 that connects the first pulley 61, the second pulley 62, and the third pulley 63 are separately disposed, will be described. However, example embodiments are not limited thereto.

The first auxiliary link 650 may connect the first pulley 61 and the third pulley 63. The second auxiliary link 651 may connect the third pulley 63 and the second pulley 62. Therefore, the third pulley 63 may be connected to the first pulley 61 and the second pulley 62 using the first auxiliary link 650 and the second auxiliary link 651.

One side of the first auxiliary link 650 may be pivotally connected to the first main link 640, and the other side of the first auxiliary link 650 may be pivotally connected to the third pulley 63. The one side of the first auxiliary link 650, the first pulley 61, and the first main link 640 may be rotated around a first rotation shaft 660 that passes through the one side of the first auxiliary link 650, the first pulley 61, and the first main link 640. Similarly, the other side of the first auxiliary link 650 and the third pulley 63 may be rotated around a third rotation shaft 662 that passes through the other side of the first auxiliary link 650 and the third pulley 63.

One side of the second auxiliary link 651 may be connected to the third pulley 63, and the other side of the second auxiliary link 651 may be pivotally connected to the second main link 641. The one side of the second auxiliary link 651 and the third pulley 63 may be rotated around the third rotation shaft 662. Similarly, a second rotation shaft 661 may pass through the other side of the second auxiliary link 651, the second pulley 62, and the second main link 641. The second main link 641 and the second pulley 62 are confined with respect to each other and thus may be together rotated around the second rotation shaft 661.

A first end W3 or a second end W4 of the first wire 503 connected to the driving source is pulled so that the knee joint 6 may be pivoted. For example, when the second frame 52 is pivoted around the knee joint 6 in a configuration in which the first frame 51 and the second frame 52 of the walking assistance robot 5 are disposed in a straight line, the second end W4 of the first wire 503 may be pulled by the driving source. If the second end W4 of the first wire 503 is pulled by the driving source, the second frame 52 may be pivoted in one direction so that the knee of the user who wears the walking assistance robot 5 may be bent. If the first end W3 of the first wire 503 is pulled by the driving source, the second frame 52 may be pivoted in another direction so that the knee of the user who wears the walking assistance robot 5 may be stretched.

If the second end W4 of the first wire 503 is pulled by the driving source, the driving pulley 60 may be rotated around the first rotation shaft 660 in a counterclockwise direction A2. The first pulley 61 may be rotated along with the driving pulley 60 around the first rotation shaft 660 in the counterclockwise direction A2. If the first pulley 61 is rotated in the counterclockwise direction A2, the second wire 504 wound around the first pulley 61 is rotated in the counterclockwise direction A2 together with the first pulley 61. The third pulley 63 on which the second wire 504 is wound, is rotated around the third rotation shaft 662 in the counterclockwise direction A2 together with the second wire 504, and the second pulley 62 on which the second wire 504 is wound, is also rotated around the second rotation shaft 661 in the counterclockwise direction A2. As a result, the second main link 641 confined with the second pulley 62 and the second frame 52 connected to the second main link 641 are rotated in the counterclockwise direction A2.

A sliding motion may occur in addition to the rotation motion. As illustrated in FIG. 8B, if the first pulley 61 is rotated around the first rotation shaft 660 in the counterclockwise direction A2, the third pulley 63 may be rotated around the third rotation shaft 662 in the counterclockwise direction A2 and simultaneously may slide along a circumference of the first pulley 61 in a counterclockwise direction A2'. Therefore, the position of the third rotation shaft 662 may be moved in the counterclockwise direction A2'.

Further, if the third pulley 63 is rotated along the circumference of the first pulley 61 in the counterclockwise direction A2', the second pulley 62 may be rotated around the second rotation shaft 661 in the counterclockwise direction A2 and simultaneously may slide along a circumference of the third pulley 63 in the counterclockwise direction A2' together with the third pulley 63. In other words, the position of the second rotation shaft 661 may be moved in the counterclockwise direction A2'. One side of the second main link 641 connected to the second pulley 62 may be moved in the counterclockwise direction A2' together with the second pulley 62, and one side of the second frame 52 connected to the second main link 641 may be moved in the counterclockwise direction A2' together with the second main link 641.

In this way, the second end W4 of the first wire 503 is pulled by the driving source so that the driving force transferred to the driving pulley 60 may be transferred to the second main link 641 and the second frame 52 through the first pulley 61, the third pulley 63, and the second pulley 62, and the first frame 51 and the second frame 52 may be moved with 2 degrees of freedom at which rotation and sliding motions may be made.

As described above, if the second end W4 of the first wire 503 is pulled, the third pulley 63 may be rotated around the third rotation shaft 662 in the counterclockwise direction A2, and the position of the third rotation shaft 662 of the third pulley 63 may be moved along the circumference of the first pulley 61. Also, the second pulley 62 may be rotated around the second rotation shaft 661 in the counterclockwise direction A2, and the position of the second rotation shaft 661 of the second pulley 62 may be moved along the circumference of the third pulley 63. In this case, a distance (see L2 of FIG. 8B) between the first rotation shaft 660 and the second rotation shaft 661 after the second frame 52 is pivoted, is greater than a distance (see L1 of FIG. 8A) between the first rotation shaft 660 and the second rotation shaft 661 before the second frame 52 is pivoted. In this way, when the second frame 52 is pivoted in the counterclockwise direction A2, a rotation center of the knee joint 6 changes so that the knee joint 6 of the walking assistance robot 5 may make a similar motion to that of the actual knee joint of the user.

As illustrated in FIG. 8B, when the second frame 52 is pivoted in the clockwise direction A1 in a configuration in which the first frame 51 and the second frame 52 form a desired (or, alternatively, a predetermined) angle, a first end W3 of the first wire 503 may be pulled by the driving source. In other words, when the bent knee of the user who wears the walking assistance robot 5 is stretched, the first end W3 of the first wire 503 may be pulled by the driving source.

When one end W3 of the first wire 503 is pulled by the driving source, the knee joint 6 may be moved in an opposite direction to a direction of the case where the other end W4 of the first wire 503 is pulled. Therefore, the driving pulley 60 is rotated around the first rotation shaft 660 in the clockwise direction A. Further, the first pulley 61 may be rotated together with the driving pulley 60 around the first rotation shaft 660 in the clockwise direction A1.

When the first pulley 61 is rotated in the clockwise direction A1, the second wire 504 wound around the first pulley 61 may be rotated in the clockwise direction A1 together with the first pulley 61. Therefore, the third pulley 63 on which the second wire 504 is wound, may be rotated around the third rotation shaft 662 in the clockwise direction A1, Further, because the second wire 504 is also wound around the second pulley 62, the second pulley 62 may also rotate around the second rotation shaft 661 in the clockwise direction A1. As a result, the second main link 641 confined with the second pulley 62 and the second frame 52 connected to the second main link 641 are rotated in the clockwise direction A1.

As illustrated in FIG. 8A, a sliding motion may occur in addition to the rotation motion. In detail, if the first pulley 61 is rotated around the first rotation shaft 660 in the clockwise direction A1, the third pulley 63 may slide along the circumference of the first pulley 61 in a clockwise direction A1'. As the third pulley 63 slides, the second pulley 62 connected to the third pulley 63 using the second wire 504 may also slide along the circumference of the third pulley 63 in the clockwise direction A1'. One side of the second main link 641 connected to the second pulley 62 may move together with the second pulley 62, and one side of the second frame 52 connected to the second main link 641 may move together with the second main link 641.

For example, if the first end W3 of the first wire 503 is pulled, the third pulley 63 may rotate around the third rotation shaft 662 in the clockwise direction A1, and the position of the third rotation shaft 662 of the third pulley 63 may be moved along the circumference of the first pulley 61. The second pulley 62 may rotate around the second rotation shaft 661 in the clockwise direction A1, and the second rotation shaft 661 of the second pulley 62 may be moved along the circumference of the third pulley 63. In this case, a distance L1 (see FIG. 8A) between the first rotation shaft 660 and the second rotation shaft 661 after the second frame 52 is pivoted, may be smaller than a distance L2 (see FIG. 8B) between the first rotation shaft 660 and the second rotation shaft 661 before the second frame 52 is pivoted. In this way, the position of a rotation center of the knee joint 6 of the walking assistance robot 5 may change. When the second frame 52 is pivoted in the clockwise direction, the position of the rotation center of the knee joint 6 changes so that the knee joint 6 of the walking assistance robot 5 may make a similar motion to that of the actual knee joint of the user.

A driving force transferring structure using a plurality of pulleys and a wire described above can transfer a relatively large driving force and can prevent a backlash from occurring. The wire that connects the plurality of pulleys may be wound a plurality of times. The wire wound a plurality of times so as to increase the driving force transferred to the pulleys serves as a decelerator and may increase the driving force transferred to the pulleys.

Figure 9A:
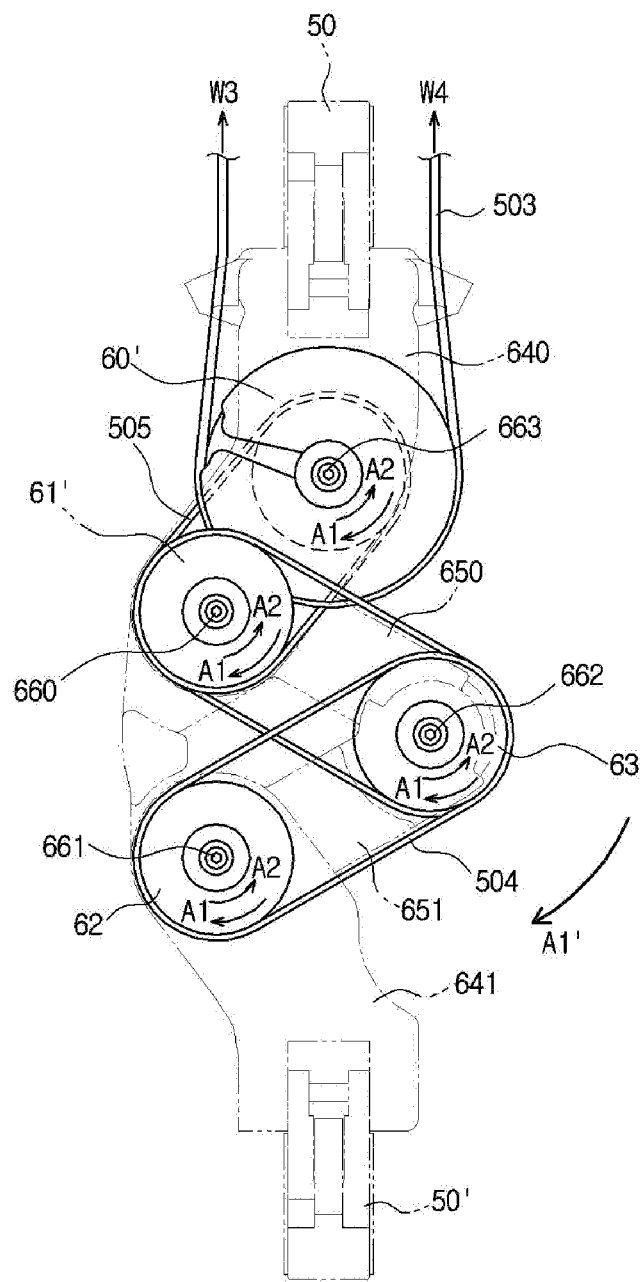
FIGS. 9A and 9B are views for describing a motion of a knee joint and a driving force transferring structure according to some example embodiments.
Figure 9B:
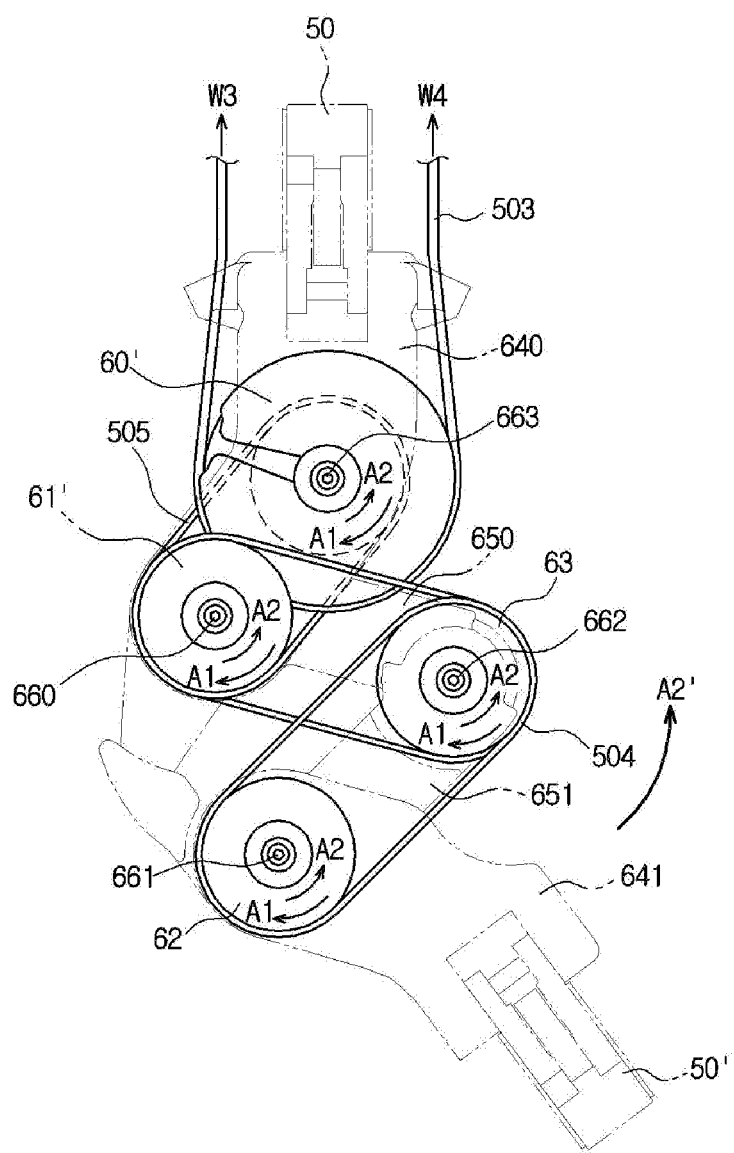

FIGS. 9A and 9B are views for describing a motion of a knee joint and a driving force transferring structure according to other example embodiments.

Referring to FIGS. 9A and 9B, rather than forming the driving pulley 60 and the first pulley 61 as a single double pulley, the knee joint 6 may include a driving pulley 60' and a first pulley 61' that are separately disposed.

For example, the first wire 503 connected to the driving source may be wound on the driving pulley 60', and the driving pulley 60' and the first pulley 61' may be connected to each other using a third wire 505.

The third wire 505 may be wound around the driving pulley 60' and the first pulley 61' and may transfer the driving force transferred to the driving pulley 60' to the first pulley 61'. Also, the first pulley 61', the second pulley 62, and the third pulley 63 may be connected to one another using the second wire 504, similarly to the example embodiment illustrated in FIGS. 6A through 8B.

Although FIGS. 9A and 9B illustrate separate wires utilized as the first through third wires 503 to 505, the first wire 503, the second wire 504 and/or the third wire 505 may be disposed as one wire.

In the knee joint 6 illustrated in FIGS. 9A and 9B, the driving pulley 60' and the first pulley 61' of the knee joint 6 are separately disposed, and a driving force transferring structure in which the driving pulley 60' and the first pulley 61' are connected to each other using the third wire 505, is different from that of the embodiment illustrated in FIGS. 6A through 8B.

The first end W3 or the second end W4 of the first wire 503 is pulled by the driving source so that the knee joint 6 makes sliding and rolling motions simultaneously and a pivoting motion is performed, similarly to the example embodiment illustrated in FIGS. 6A through 8B. However, as discussed above, in the example embodiment illustrated in FIGS. 9A and 9B, the driving pulley 60' and the first pulley 61' are connected to each other using the third wire 505 in the driving force transferring structure.

Figure 10A:
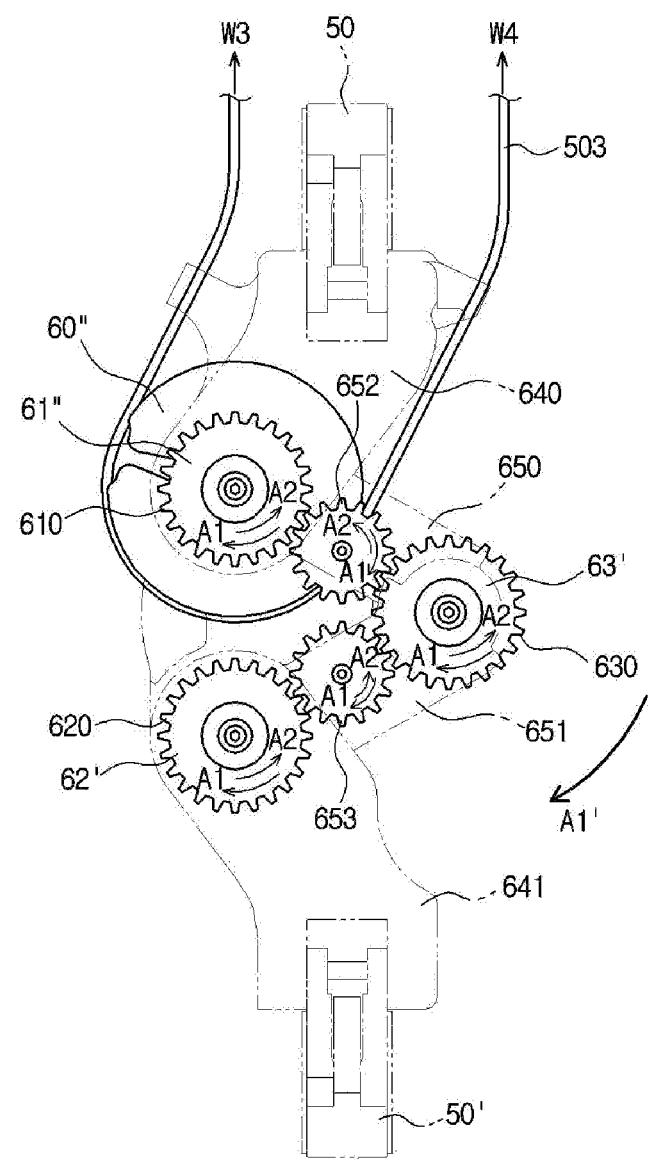
FIGS. 10A and 10B are views for describing a motion of a knee joint and a driving force transferring structure according to other example embodiments.
Figure 10B:
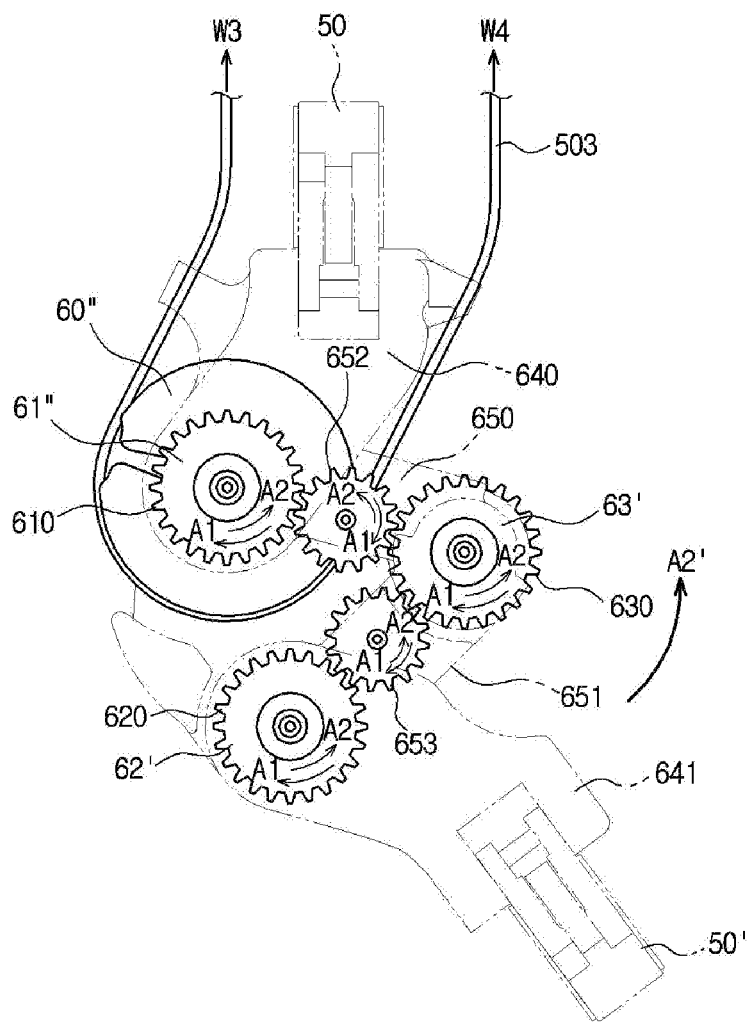

FIGS. 10A and 10B are views for describing a motion of a knee joint and a driving force transferring structure according to still other example embodiments.

Referring to FIGS. 10A and 10B, to further increase the driving force, in other example embodiments driving pulleys may be connected to each other using a planetary gear. For example, in the knee joint 6, a driving force may be transferred to a driving pulley 60" through gear connection so that the second frame 52 may be pivoted. The driving force may be transferred to the driving pulley 60" using the first wire 503 connected to the driving source.

The first pulley 61" may be formed integrally with the driving pulley 60", or may be separately formed and connected to the driving pulley 60" using a wire.

A first gear 610 may be formed on an outer circumferential surface of the first pulley 61", and a second gear 620 may be formed on an outer circumferential surface of the second pulley 62', and a third gear 630 may be formed on an outer circumferential surface of the third pulley 63'. A first auxiliary gear 652 may be disposed between the first pulley 61" and the third pulley 63' and may be engaged with the first gear 610 and the third gear 630. A second auxiliary gear 653 may be disposed between the second pulley 62' and the third pulley 63' and may be engaged with the second gear 620 and the third gear 630.

If the second end W4 of the first wire 503 is pulled, the driving pulley 60" may rotate in a counterclockwise direction A2, and, therefore, the first pulley 61" may also be rotated in the counterclockwise direction A2. If the first pulley 61" is rotated in the counterclockwise direction A2, the first auxiliary gear 652 engaged with the first gear 610 may rotate in a clockwise direction A1. If the first auxiliary gear 652 is rotated in the clockwise direction A1, the third gear 630 engaged with the first auxiliary gear 652 may rotate in the counterclockwise direction A2. Since the third gear 630 is engaged with the first auxiliary gear 652 and is rotated, the third gear 630 may be moved along the circumference of the first auxiliary gear 652 and simultaneously may be rotated in the counterclockwise direction A2.

If the third gear 630 is rotated in the counterclockwise direction A2, the second auxiliary gear 653 engaged with the third gear 630 may rotate in the clockwise direction A1. If the second auxiliary gear 653 is rotated in the clockwise direction A1, the second gear 620 may also rotate in the counterclockwise direction A2. Since the second auxiliary gear 653 is engaged with the third gear 630 and is rotated, the second auxiliary gear 653 may be moved along the circumference of the third gear 630 and simultaneously may be rotated in the counterclockwise direction A2. Since the second gear 620 is also engaged with the second auxiliary gear 653 and is rotated, the second gear 620 may be moved along the circumference of the second auxiliary gear 653 and simultaneously may be rotated in the counterclockwise direction A2.

If the second gear 620 is rotated in the counterclockwise direction A2, the second main link 641 on which the second pulley 62' is mounted, and the second frame 52 connected to the second main link 641 may be pivoted in the counterclockwise direction A2. Through this gear connection, the second frame 52 may be rotated and pivoted.

When the first end W3 of the first wire 503 is pulled, a rotation direction of the first gear 610, the second gear 620, the third gear 630, the first auxiliary gear 652, and the second auxiliary gear 653 may be opposite to a rotation direction when the second end W4 of the first wire 503 is pulled, and a rotation center of the second frame 52 may change, and the second frame 52 may make a pivoting motion in which it is rotated in the clockwise direction A1.

Figure 11A:
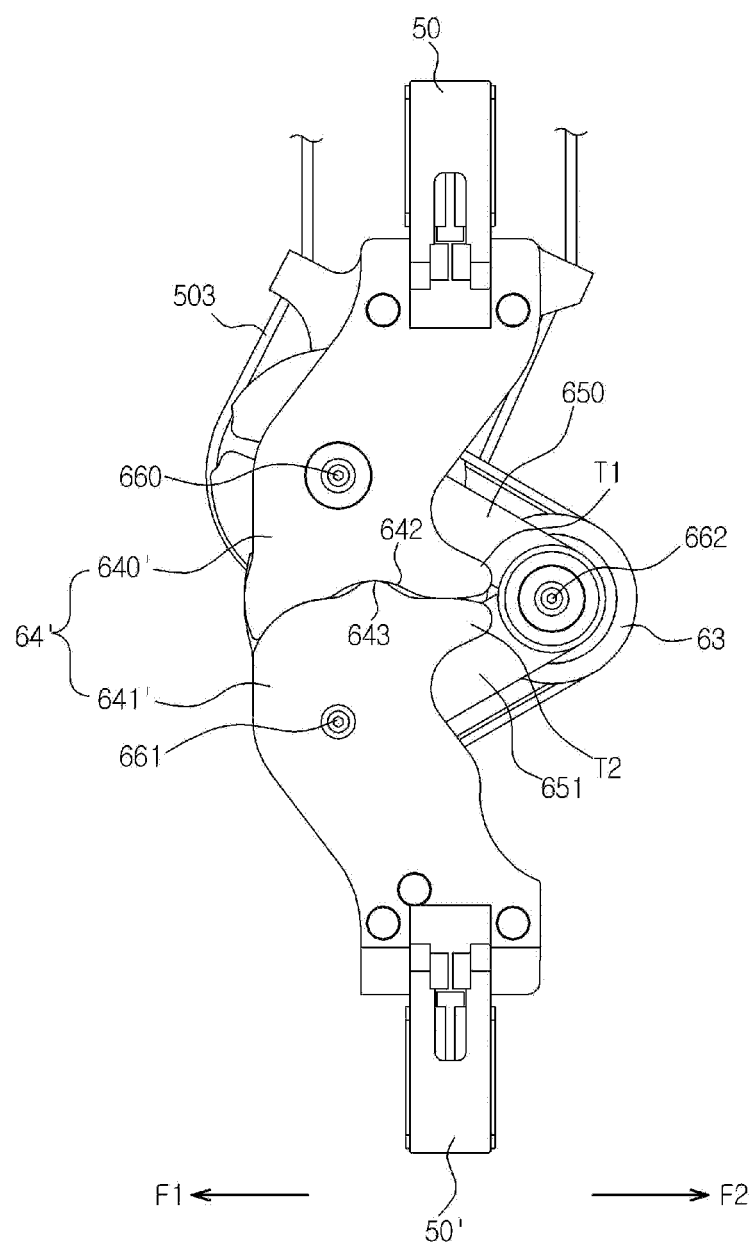
FIGS. 11A and 11B are views for describing a load supporting structure according to a motion of a knee joint according to other example embodiments.
Figure 11B:
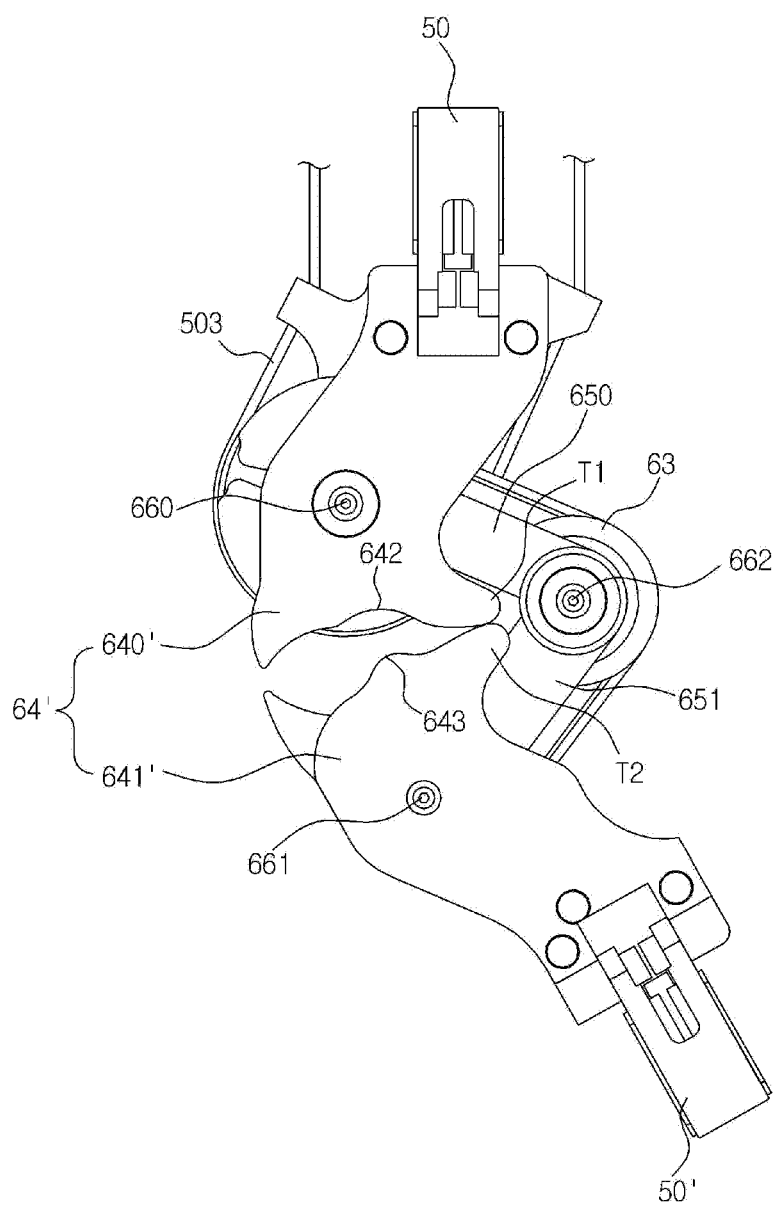

FIGS. 11A and 11B are views for describing a load supporting structure according to a motion of a knee joint according to yet still other example embodiments.

Referring to FIGS. 11A and 11B, a main link 64' of the knee joint 6 may support the user's load through surface contact. That is, one surface of the first main link 640' connected to the first frame 51 and one surface of the second main link 641' connected to the second frame 52 may be disposed to be in surface contact with each other.

A first contact surface 642 that is a lower surface of the first main link 640' may not be flat and may have a non-uniform height. For example, the first contact surface 642 of the first main link 640' may include a convex portion that protrudes downwardly and/or a concave portion that is concave in an upward direction.

A second contact surface 643 that is an upper surface of the second main link 641' may be formed to have a shape corresponding to the first contact surface 642 of the first main link 640'. For example, a convex portion corresponding to the concave portion formed on the first contact surface 642 of the first main link 640' may be formed on the second contact surface 643 of the second main link 641'. Likewise, if the first contact surface 642 has a convex portion, the second contact surface 643 may have a concave portion corresponding thereto.

As illustrated in FIG. 11A, when the first frame 51 and the second frame 52 of the walking assistance robot 5 extend in a straight line, the second main link 641' may support the first main link 640' using the first contact surface 642 of the first main link 640' and the second contact surface 643 of the second main link 641' that contact each other. If the user wears the walking assistance robot 5 and the user's load is applied to the knee joint 6, the first main link 640' may be supported by the second main link 641' so that the load applied to the knee joint 6 may be supported.

A first guide portion T1 may be disposed at one side of the first contact surface 642 of the first main link 640'. The first guide portion T1 may face the third pulley 63 when the first frame 51 and the second frame 52 extend in a straight line. For example, if a direction toward the third pulley 63 based on the first frame 51 and the second frame 52 is referred to as a backward direction F2 and an opposite direction to the direction toward the third pulley 63 is referred to as forward direction F1, the first guide portion T1 may be disposed in the backward direction F2. The first guide portion T1 may be convex in a downward direction. Similarly, a second guide portion T2 may be disposed at one side of the second contact surface 643 of the second main link 641' so as to be in the backward direction F2. The second guide portion T2 may be convex in an upward direction.

As illustrated in FIG. 11B, if the first frame 51 of the second frame 52 is pivoted around the knee joint 6, front portions of the first contact surface 642 and the second contact surface 643 may be spaced apart from each other. However, the first guide portion T1 that is downwardly convex may be supported by the second guide portion T2 when a contact point between the first guide portion T1 and the second guide portion T2 that is upwardly convex changes. Thus, even when the first frame 51 or the second frame 52 is pivoted around the knee joint 6, the bottom surface of the first guide portion T1 is supported by the upper surface of the second guide portion T2 so that the load applied to the knee joint 6 may be supported.

A buffer member, such as silicon or rubber, may be mounted on the first contact surface 642 and the second contact surface 643. The buffer member may alleviate a shock that occurs when the first contact surface 642 and the second contact surface 643 collide with each other and may prevent noise caused by the shock.

Figure 12A:
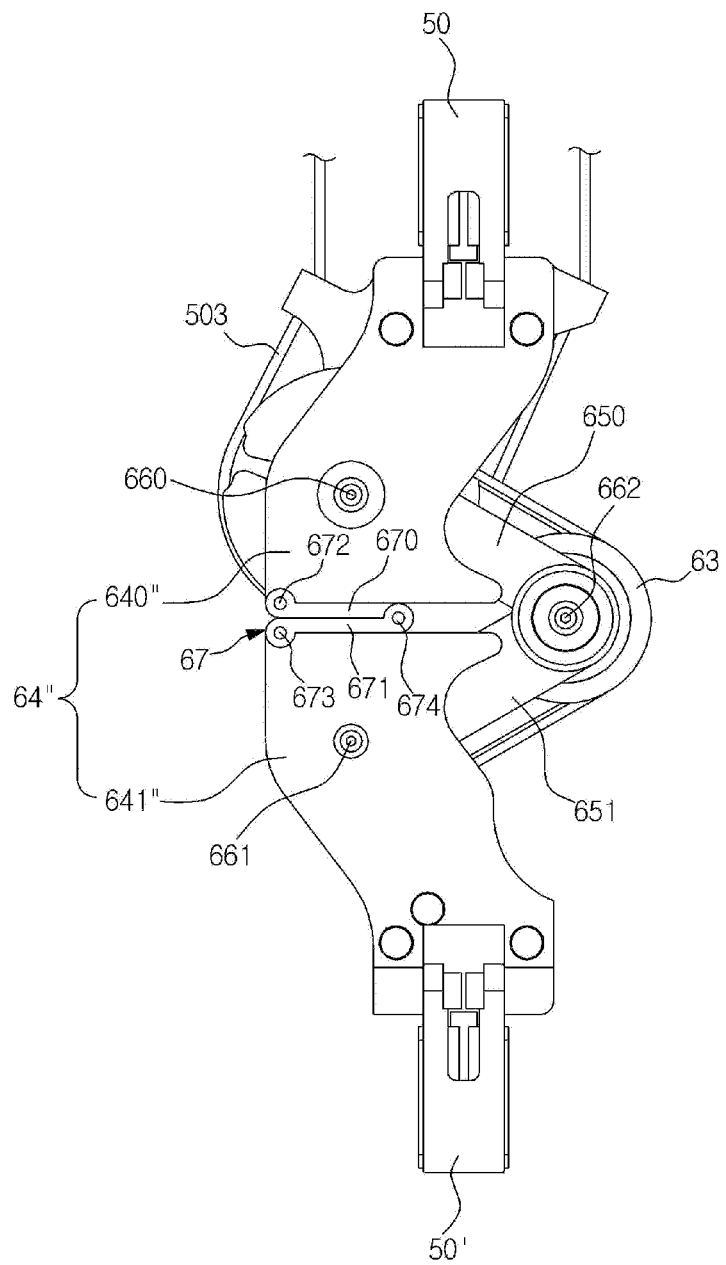
FIGS. 12A and 12B are views for describing a load supporting structure according to a motion of a knee joint according to other example embodiments.
Figure 12B:
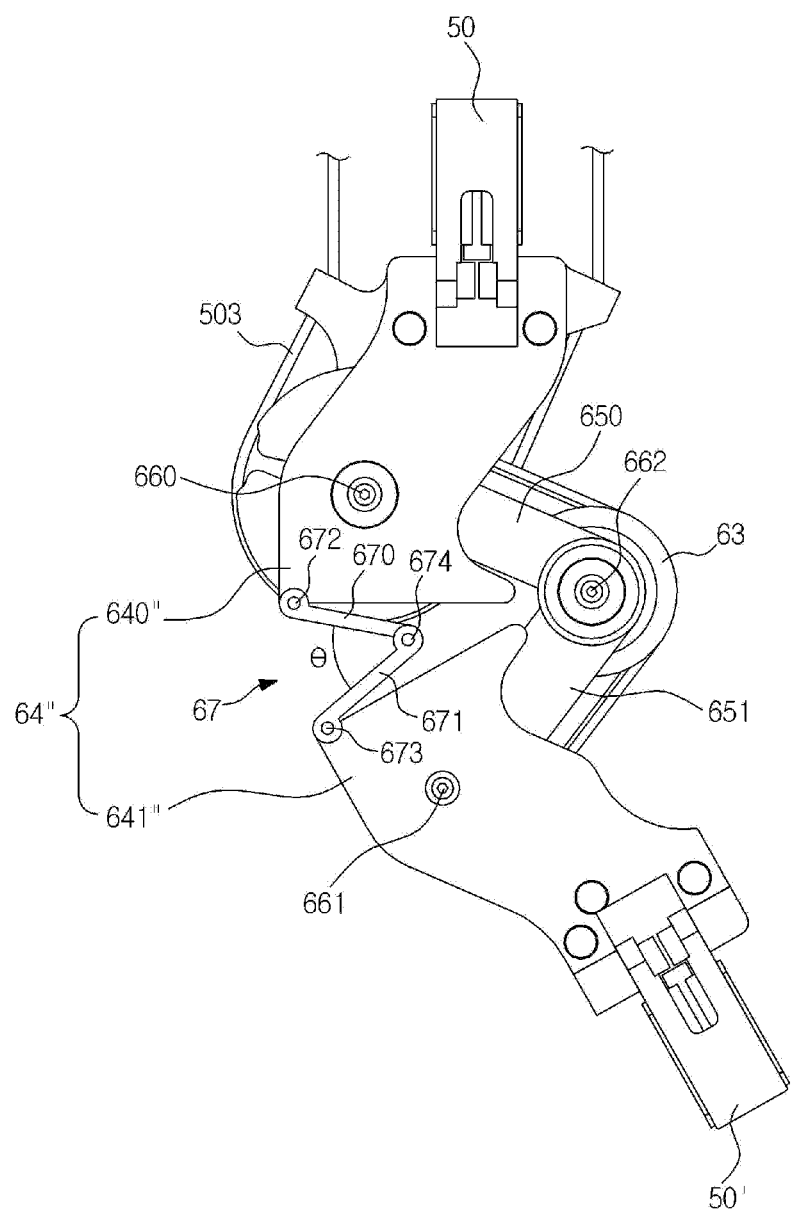

FIGS. 12A and 12B are views for describing a load supporting structure according to a motion of a knee joint according to yet still other example embodiments.

Referring to FIGS. 12A and 12B, the knee joint 6 may include a link unit 67 that connects a first main link 640" and a second main link 641". The link unit 67 may include a first support link 670 and a second support link 671. One side of the first support link 670 may be pivotally mounted on a lower portion of the first main link 640" using a first rotation shaft 672. One side of the second support link 671 may be pivotally mounted on an upper portion of the second main link 641" using a second rotation shaft 673. The other side of the first support link 670 and the other side of the second support link 671 may be pivotally connected to each other using a third rotation shaft 674.

As illustrated in FIG. 12A, the link unit 67 may be disposed between a lower surface of the first main link 640" and an upper surface of the second main link 641" when the first frame 51 and the second frame 52 extend in a straight line. In this case, an angle θ between the first support link 670 and the second support link 671 on the third rotation shaft 674 may be zero degrees or close to zero degrees.

The first support link 670 and the second support link 671 may be stacked between the first main link 640" and the second main link 641" in the vertical direction. A load applied to the knee joint 6 may be supported by the first main link 640", the second main link 641", and contact surfaces of the first support link 670 and the second support link 671 that are disposed between the first main link 640" and the second main link 641".

As illustrated in FIG. 12B, if the first frame 51 or the second frame 52 is pivoted, the lower surface of the first main link 640" may be spaced apart from the upper surface of the second main link 641". As the first frame 51 or the second frame 52 is pivoted, the angle θ between the first support link 670 and the second support link 671 may increase.

A buffer member, such as silicon or rubber, may be mounted on a surface that contacts another member to which the first main link 640", the second main link 641", the first support link 670, and the second support link 671 are adjacent, and may alleviate noise and shock that occur when these members collide with each other.

Figure 13A:
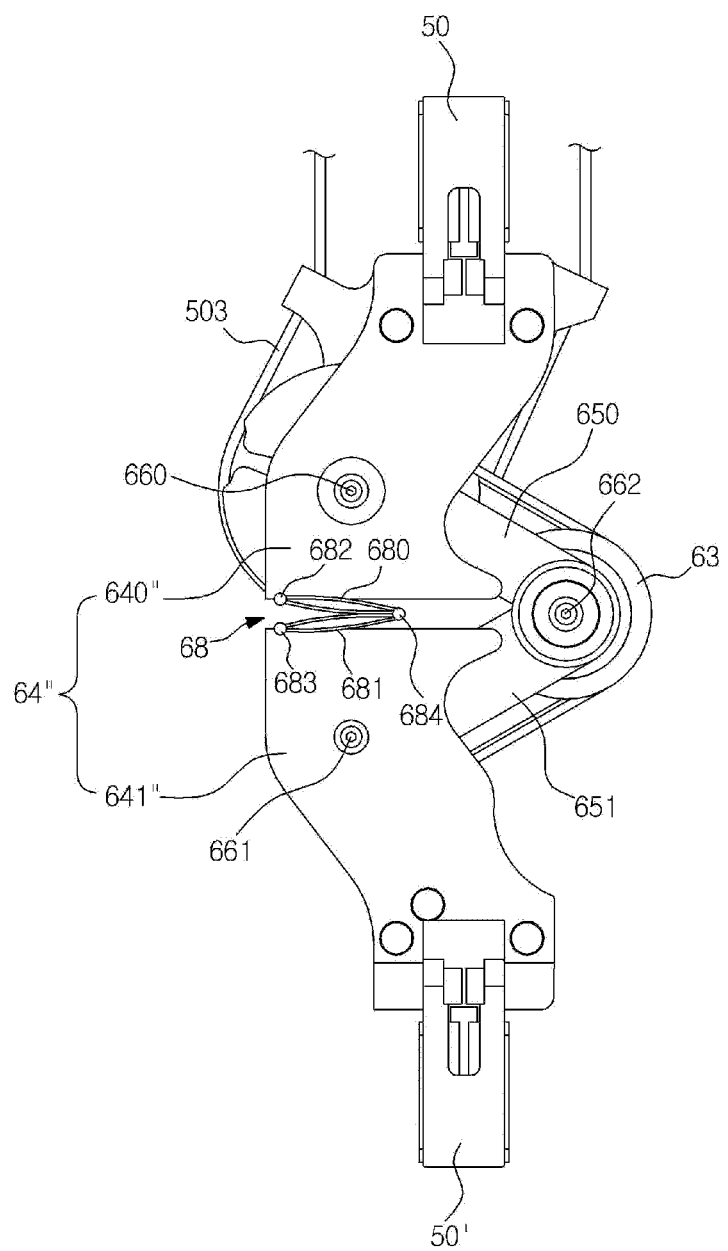
FIGS. 13A and 13B are views for describing a load supporting structure according to a motion of a knee joint according to other example embodiments.
Figure 13B:
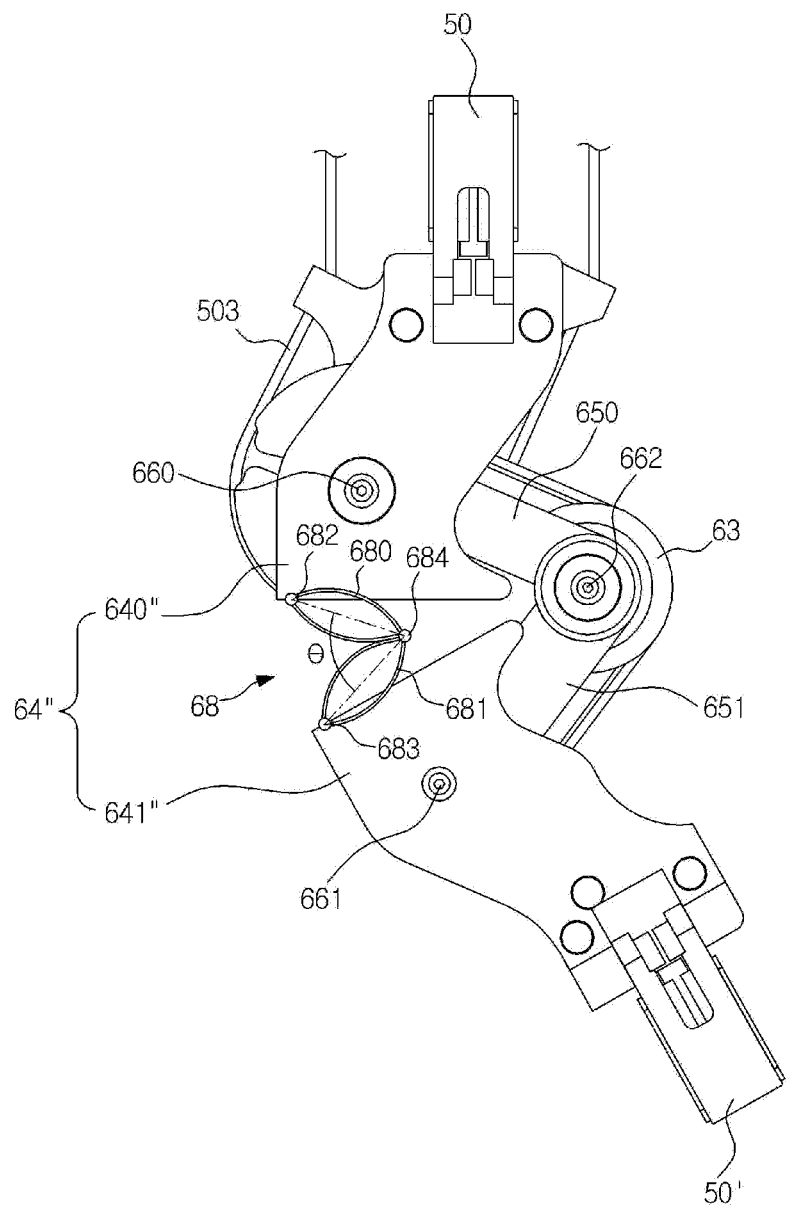

FIGS. 13A and 13B are views for describing a load supporting structure according to a motion of a knee joint according to yet still other example embodiments.

Referring to FIGS. 13A and 13B, the knee joint 6 may include an elastic unit 68 that connects the first main link 640" and the second main link 641". The elastic unit 68 may include a first elastic member 680 and a second elastic member 681. One side of the first elastic member 680 may be pivotally mounted on a lower portion of the first main link 640" using a first rotation shaft 682. One side of the second elastic member 681 may be pivotally mounted on an upper portion of the second main link 641" using a second rotation shaft 683. The other side of the first elastic member 680 and the other side of the second elastic member 681 may be pivotally connected to each other using a third rotation shaft 684.

As illustrated in FIG. 13A, the elastic unit 68 may be disposed between the lower surface of the first main link 640" and the upper surface of the second main link 641" when the first frame 51 and the second frame 52 extend in a straight line. In this case, an angle θ between the first elastic member 680 and the second elastic member 681 on the third rotation shaft 684 may be zero degrees or close to zero degrees.

The first elastic member 680 and the second elastic member 681 may be stacked between the first main link 640" and the second main link 641" in the vertical direction. A load applied to the knee joint 6 may be supported by the first main link 640", the second main link 641", and contact surfaces of the first elastic member 680 and the second elastic member 681 that are disposed between the first main link 640" and the second main link 641".

As illustrated in FIG. 13B, if the first frame 51 or the second frame 52 is pivoted, the lower surface of the first main link 640" may be spaced apart from the upper surface of the second main link 641". As the first frame 51 or the second frame 52 is pivoted, the angle θ between the first elastic member 680 and the second elastic member 681 may increase.

The first elastic member 680 and the second elastic member 681 may be leaf springs that exert an elastic force in a direction in which adjacent members are spaced apart from each other. However, example embodiments are not limited thereto. For example, the first elastic member 680 and the second elastic member 681 may be tension/extension springs, compression springs, and/or coil springs.

When the first frame 51 and the second frame 52 are pivoted and form a straight line, noise and shock that occur when the first main link 640" and the second main link 641" collide with each other, may be alleviated due to the elastic force of the first elastic member 680 and the second elastic member 681.

According to the one or more example embodiments, through the structure of a joint assembly including a plurality of pulleys and wires and/or gears, the knee joint 6, 14 of the walking assistance robot may make a similar motion to that of the actual knee joint of the user. When the user bends or stretches his/her knee, a knee joint 6, 14 of the walking assistance robot makes sliding and rolling motions simultaneously and makes the same motion as that of the actual knee joint of the user so that the user can feel comfort when he/she wears the walking assistance robot and walks. In addition, through a load supporting structure disposed on the knee joint of the walking assistance robot, a load applied to the knee joint when the user wears the walking assistance robot, can be stably supported. By using a buffer member disposed in the load supporting structure, a shock applied to the knee joint and noise caused by the shock can be alleviated.

Figure 14:
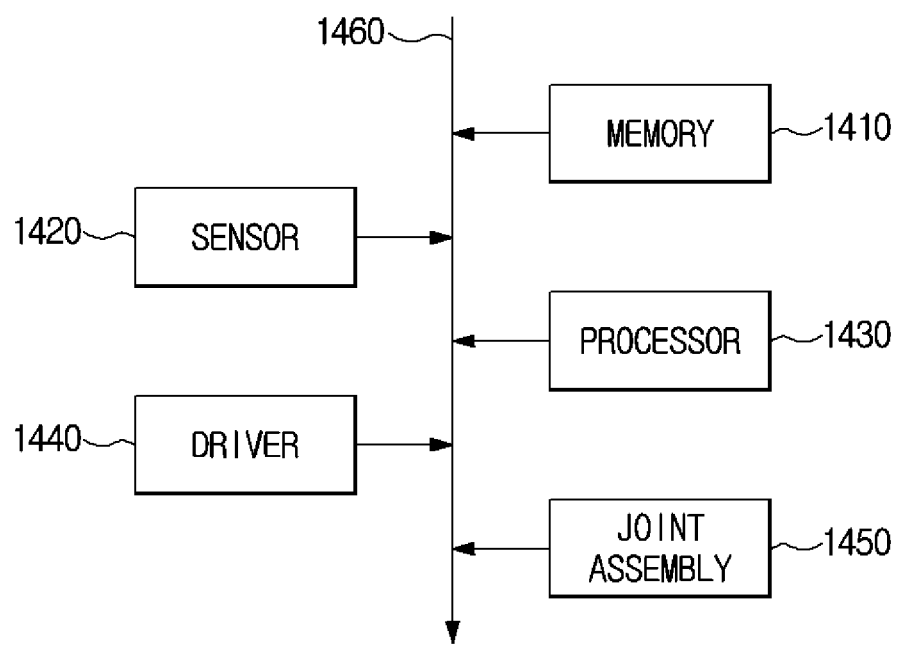
FIG. 14 illustrates a walking assistance robot according to some example embodiments.

FIG. 14 illustrates a walking assistance robot according to some example embodiments.

As illustrated in FIG. 14, a walking assistance robot may include, for example, a memory 1410, a sensor 1420, a processor 1430, a driver 1440, and a joint assembly 1450 that may send data to and/or receive data from one another using a data bus 1460.

The memory 1410 may be any device capable of storing data. For example, the memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The sensor 1420 may be configured to sense whether the user is walking. For example, the sensor 1420 may be a pressure sensor. The pressure sensor may be a ground reaction force (GRF) sensor that senses GRF transferred to the user's foot when the user walks.

The processor 1430 may be any device capable of processing data including, for example, a microprocessor configured to carry out specific operations by performing arithmetical, logical, and input/output operations based on input data, or capable of executing instructions included in computer readable code. The processor 1430 may be a logic chip, for example, a central processing unit (CPU), a controller, or an application-specific integrated circuit (ASIC), that when, executing the instructions stored in the memory 1410, configures the processor 1430 as a special purpose machine such that the processor 1430 is configured to determine an amount of tension to utilize to pull the wires associated with the joint assembly 1450 based on a result of sensing performed by the sensor 1420, and instruct the driver 1440 to pull the wires with the determined tension.

The processor 1430 may control the amount of tension provided to the wires by the driver 1440 based on a weight of a wearer of the walking assistance robot. For example, the processor 1430 may measure a weight of the wearer using the pressure sensor I 1420 installed at one or more of the foot structures 57, and adjust the amount of torque based on the sensed weight. The sensed weight may include an object that the wearer is holding.

Further still, the processor 1430 may provide a different amount of torque to the joint assembly 1450 as the wearer moves through various phases of a walking cycle. For example, the processor 1430 may instruct the walking assistance robot to increase the torque, if the joint assembly 1450 is exerting positive work on the leg, for example, when the wearer is increasing a pace of walking on a flat surface, a sloped surface or a stepped surface. Likewise, the processor 1430 may instruct the walking assistance robot to increase a damping torque applied to a leg of the wearer, if the joint assembly 1450 is exerting negative work on the leg, for example, when the wearer is decreasing a pace of walking on the flat surface, the sloped surface or the stepped surface.

The driver 1440 may be a motor that generates torque according to electric energy supplied from a power supply (not shown). The motor may be provided with an encoder. Alternatively, the driver 1440 may include at least one piston or cylinder device that is operated by electric energy or by fluidic pressure such as, for example, hydraulic pressure or pneumatic pressure generating torque. The driver 1440 may exert an amount of torque on the cables based on instructions received from the processor 1430.

The joint assembly 1450 may include wires and pulleys that move in response to the torque applied to the cables by the driver 1440 such that the joint assembly 1450 may simultaneously roll and slide to prevent misalignment between the joint assembly and a knee joint of a wearer of the walking assistance robot. Further still, one or more of the memory 1410, sensor 1420, processor 1430 and driver 1440 may be included in the joint assembly 1450.

As described above, according to one or more example embodiments, a joint assembly that makes a similar motion to that of the user's actual joint can be implemented. The joint assembly included in a walking assistance robot can support the user's load.

Although a few example embodiments of have been shown and described, it would be appreciated by those skilled in the art that changes may be made in these example embodiments without departing from the principles and spirit thereof, the scope of which is defined in the claims and their equivalents.

What is claimed is:

1. A joint assembly comprising:
    a first pulley configured to receive a driving force and perform a rotation around a first rotation shaft in response to the driving force, the first pulley being mounted on a first main link such that the first rotation shaft passes through the first pulley and the first main link, the first main link being connected to a first frame;
    a second pulley configured to rotate around a second rotation shaft in response to the rotation of the first pulley, the second pulley being mounted on a second main link such that the second rotation shaft passes through the second pulley and the second main link, the second main link being connected to a second frame;
    a third pulley configured to rotate around a third rotation shaft in response to the rotation of the first pulley, the third pulley connected to the first pulley and the second pulley;
    a first wire configured to connect a driving source and the first pulley to transmit the driving force to the first pulley; and
    at least one second wire configured to connect the first pulley, the second pulley, and the third pulley such that, in response to the driving force being transmitted to the first pulley via the first wire, the at least one second wire causes the third pulley to rotate about the third rotation shaft to adjust a rotational center of the joint assembly by changing a distance between the first rotation shaft and the second rotation shaft.

2. The joint assembly of claim 1, further comprising:
    a first gear on an outer circumferential surface of the first pulley;
    a second gear on an outer circumferential surface of the second pulley; and
    a third gear on an outer circumferential surface of the third pulley.

3. The joint assembly of claim 2, further comprising:
    a first auxiliary gear between the first pulley and the third pulley such that the first auxiliary gear is configured to engage with the first gear and the third gear; and
    a second auxiliary gear between the third pulley and the second pulley such that the second auxiliary gear is configured to engage with the third gear and the second gear.

4. The joint assembly of claim 1, further comprising:
    a driving pulley connected to the first pulley, wherein
        the first wire is connected to the driving pulley such that the driving force transferred to the driving pulley is transferred to the first pulley.

5. The joint assembly of claim 4, wherein the first pulley is integrated with the driving pulley.

6. The joint assembly of claim 1, wherein
    the first main link has a first side and a second side, the first pulley being mounted on the first side of the first main link and the first frame connected to the second side of the first main link; and
    the second main link has a first side and a second side, the second pulley being mounted on the first side of the second main link and the second frame connected to the second side of the second main link.

7. The joint assembly of claim 6, further comprising:
    a first auxiliary link configured to connect the first main link and the third pulley; and
    a second auxiliary link configured to connect the third pulley and the second main link.

8. The joint assembly of claim 7, wherein
    a first end of the first auxiliary link, the first main link, and the first pulley have the first rotation shaft passing therethrough,
    a first end of the second auxiliary link, the second main link, and the second pulley have the second rotation shaft passing therethrough, and
    a second end of the first auxiliary link, the third pulley, and a second end of the second auxiliary link have the third rotation shaft passing therethrough.

9. The joint assembly of claim 6, wherein
    the first main link has a lower surface that is configured to make surface contact with an upper surface of the second main link such that the second main link supports the first main link when the first frame and the second frame extend in a straight line,
    the lower surface of the first main link has a non-uniform shape, and
    a shape of the upper surface of the second main link corresponds to the non-uniform shape of the lower surface of the first main link.

10. The joint assembly of claim 6, wherein a first guide portion is formed at one of the first and second side of the first main link, and a second guide portion is formed at one of the first and second side of the second main link such that, when the first frame or the second frame pivots, the second guide portion is configured to support the first guide portion.

11. The joint assembly of claim 6, wherein the first main link and the second main link contact each other at a contact surface thereof, and the joint assembly further comprises:
    a buffer member on the contact surface, the buffer member formed of material including one or more of silicon and rubber.

12. The joint assembly of claim 6, further comprising:
    a link configured to pivotally connect the first main link and the second main link such that, if the first frame and the second frame extend in a straight line, the link is disposed between the first main link and the second main link.

13. The joint assembly of claim 6, further comprising:
    an elastic link configured to pivotally connect the first main link and the second main link such that, if the first frame and the second frame extend in a straight line, the elastic link is disposed between the first main link and the second main link.

14. A walking assistance robot comprising:
    a first frame configured to mount on a thigh; and
    a second frame configured to mount on a calf, the second frame connected to the first frame via a knee joint assembly, the knee joint assembly including,
        a first pulley on a first main link such that a first rotation shaft passes through the first pulley and the first main link, the first main link being connected to a first, the first main link mounted on the first frame such that, if a driving force is transferred to the first pulley, the first pulley is configured to perform a rotation about the first rotation shaft in a first direction, a second pulley mounted on a second main link such that a second rotation shaft passes through the second pulley and the second main link, the second main link mounted on the second frame, the second pulley configured to rotate about the second rotation shaft, a third pulley configured to rotate around a third rotation shaft in response to the rotation of the first pulley, the third pulley connected to the first pulley and the second pulley, a first wire configured to connect a driving source and the first pulley to transmit the driving force to the first pulley, and at least one second wire configured to connect the first pulley, the second pulley, and the third pulley such that, in response to the driving force being transmitted to the first pulley via the first wire, the at least one second wire causes the third pulley to rotate about the third rotation shaft to adjust a rotational center of the knee joint assembly by changing a distance between the first rotation shaft and the second rotation shaft.

15. The walking assistance robot of claim 14, wherein the second main link is configured to support the first main link such that the knee joint assembly is configured to support a load is applied to one or more of the first frame and the second frame.

16. The walking assistance robot of claim 14, further comprising:
a link configured to connect the first main link and the second main link, the link including,
a first support link pivotally mounted on the first main link; and
a second support link pivotally mounted on the second main link and the first support link.

17. The walking assistance robot of claim 16, wherein, if the first frame and the second frame extend in a straight line, the first support link and the second support link are configured to fold such that the first support link and the second support link are disposed between the first main link and the second main link to support a load applied to the knee joint assembly.

18. A joint assembly configured to connect a first frame and a second frame that are configured to respectively mount on upper and lower portions of a leg of a wearer, the joint assembly comprising:

a first pulley configured to receive a driving force and perform a rotation around a first shaft in response to the driving force, the first pulley being mounted on a first main link such that the first shaft passes through the first pulley, the first main link and a first end of a first auxiliary link, the first main link being connected to the first frame;

a second pulley configured to rotate around a second shaft in response to the rotation of the first pulley, the second pulley being mounted on a second main link such that the second shaft passes through the second pulley, the second main link, a second end of the first auxiliary link and a first end of a second auxiliary link, the second main link being connected to the second frame;

a third pulley configured rotate around a third shaft formed in the second frame and a second end of the second auxiliary link in response to the rotation of the first pulley;

a first wire configured to connect a driving source and the first pulley to transmit the driving force to the first pulley; and at least one second wire configured to connect the first pulley, the second pulley, and the third pulley such that, in response to the driving force being transmitted to the first pulley via the first wire, the at least one second wire causes the third pulley to rotate about the third shaft to adjust a rotational center of the joint assembly by changing a distance between the first shaft and the second shaft.

19. The joint assembly of claim 18, further comprising:
a driver configured to pull the first wire such that the first, second and third pulleys rotate in a same direction while a rotational center of the second shaft and the third shaft move relative to the first pulley.

20. The joint assembly of claim 19, further comprising:
a processor configured to instruct the driver to pull the first wire with an amount of tension determined based on one or more of a weight of a wearer of the joint assembly and a current phase of a walking cycle of the wearer.

21. The joint assembly of claim 18, wherein the joint assembly is configured to simultaneously roll and slide such that the first frame and second frame maintain alignment with the upper portion and the lower portion of the leg of the wearer, respectively, when the joint assembly bends.

* * * * *